US011827663B2

(12) United States Patent
Yarema et al.

(10) Patent No.: US 11,827,663 B2
(45) Date of Patent: Nov. 28, 2023

(54) USE OF UAP INHIBITORS TO INHIBIT FLUX THROUGH THE HEXOSAMINE BIOSYNTHETIC PATHWAY

(71) Applicant: The Johns Hopkins University, Baltimore, MD (US)

(72) Inventors: Kevin J. Yarema, Woodstock, MD (US); Christopher T. Saeui, Rockville, MD (US); Alfredo Quinones-Hinojosa, Bel Air, MD (US); Sagar Ramesh Shah, Clemson, SC (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/127,979

(22) Filed: Dec. 18, 2020

(65) Prior Publication Data

US 2021/0269468 A1   Sep. 2, 2021

Related U.S. Application Data

(62) Division of application No. 15/503,911, filed as application No. PCT/US2015/045200 on Aug. 14, 2015, now Pat. No. 10,899,784.

(60) Provisional application No. 62/037,745, filed on Aug. 15, 2014.

(51) Int. Cl.
| | |
|---|---|
| *A61K 31/7008* | (2006.01) |
| *A61K 31/7024* | (2006.01) |
| *C07H 13/04* | (2006.01) |
| *A61K 45/06* | (2006.01) |
| *A61K 31/35* | (2006.01) |
| *C07H 13/08* | (2006.01) |
| *C12Q 1/48* | (2006.01) |

(52) U.S. Cl.
CPC ............. *C07H 13/04* (2013.01); *A61K 31/35* (2013.01); *A61K 31/7024* (2013.01); *A61K 45/06* (2013.01); *C07H 13/08* (2013.01); *C12Q 1/485* (2013.01); *C12Y 207/07023* (2013.01); *C12Y 207/07083* (2015.07); *G01N 2333/9125* (2013.01); *G01N 2500/04* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 2010/0016386 A1 | 1/2010 | Vocadlo et al. | |
| 2011/0206734 A1* | 8/2011 | Yarema | C07H 15/04 435/375 |

OTHER PUBLICATIONS

Du, Jian, et al., "Carbohydrate engineered cells for regenerative medicine", Advanced Drug Delivery Reviews, 2010, vol. 62, No. 7, pp. 671-682.
National Center for Biotechnology Information. PubChem Substance Database; SID=118189839, May 3, 2011, Retrieved from the Internet, <URL: https://pubchem.ncbi.nim.nih.gov/substance/118189839>.
Liberek, Beata, et al., "N-Alkyl derivatives of 2-amino-2-deoxy-D-glucose", Carbohydrate Research, 2005, vol. 340, No. 11, pp. 1876-1884.
The International Search Report issued in corresponding International Application No. PCT/US2015/045200, dated Nov. 25, 2015, 4 pages.
The Written Opinion of the International Searching Authority issued in corresponding International Application No. PCT/US2015/045200, dated Nov. 25, 2015, 9 pages.
Inch, et al., "N-Acyl Derivatives of 2-Acylamino-2-deoxyhexoses. The Rearrangement of 2-(N-Acetylbenzamido)-2-deoxy-D-Glucose," National Institute of Arthritis and Metabolic Diseases, National Institutes of Health, Public Hlth Svs., vol. 31, pp. 1821-1825, 1966.

* cited by examiner

*Primary Examiner* — Traviss C McIntosh, III
(74) *Attorney, Agent, or Firm* — Fox Rothschild LLP

(57) ABSTRACT

Disclosed are UAP inhibitors to inhibit glucose flux in the hexosamine biosynthetic pathway and methods of treating a disease using the inhibitors.

20 Claims, 26 Drawing Sheets

$R_1$, $R_2$, $R_3$, $R_4$, $R_5$ = -H, -CH$_n$CH$_3$ where n= 0-6 including branched alkyls, -Br, -Cl, -F, -I, -NH$_2$, -SH, -NO$_2$, -NHSO$_2$R where R is alkyl or branched alkyl, -SO$_2$NHR where R is alkyl or branched alkyl, -OH, -OR where R is alkyl or branched alkyl or alkyl ester, -NHR where R is alkyl or branched alkyl or amide, -OCF$_3$, -COOH, -COOR where R is alkyl or branched alkyl R$_1$, R$_2$, R$_3$, R$_4$, R$_5$ = -H, -CH$_n$CH$_3$ where n= 0-6 including branched alkyls, -Br, -Cl, -F, -I, -NH$_2$, -SH, -NO$_2$, -NHSO$_2$R where R is alkyl or branched alkyl, -SO$_2$NHR where R is alkyl or branched alkyl, -OH, -OR where R is alkyl or branched alkyl or alkyl ester, -NHR where R is alkyl or branched alkyl or amide, -OCF$_3$, -COOH, -COOR where R is alkyl or branched alkyl $R_5$ = alkyl (branched or unbranched) that may or may not contain heteroatoms NH, O, or S

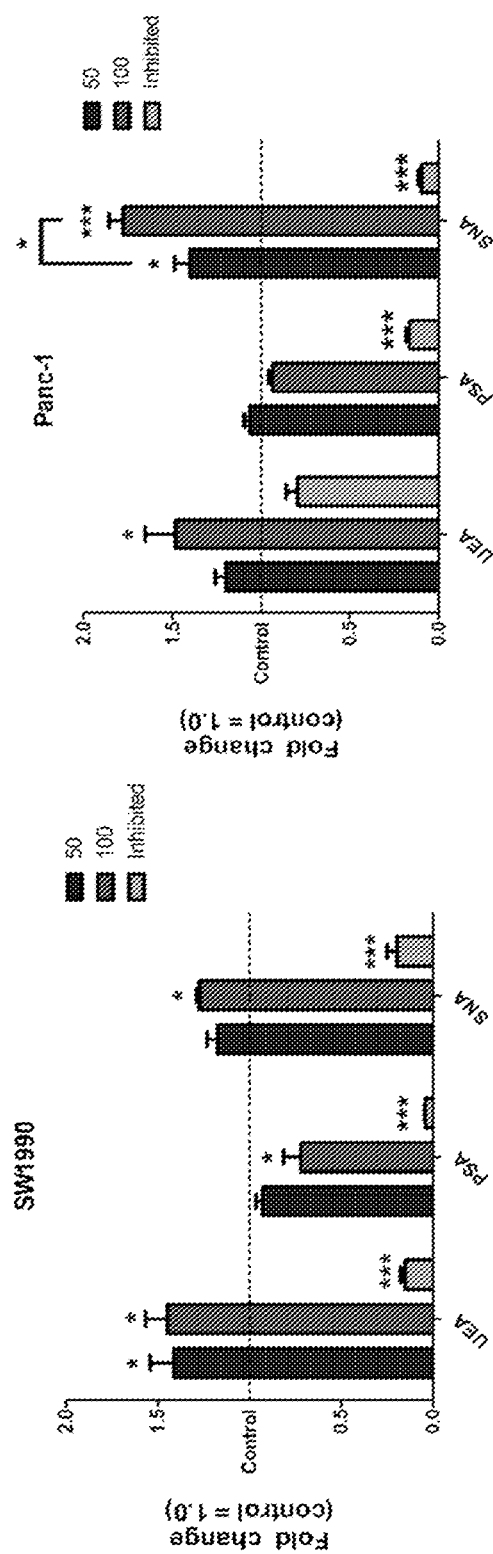
FIG. 19A
FIG. 19B
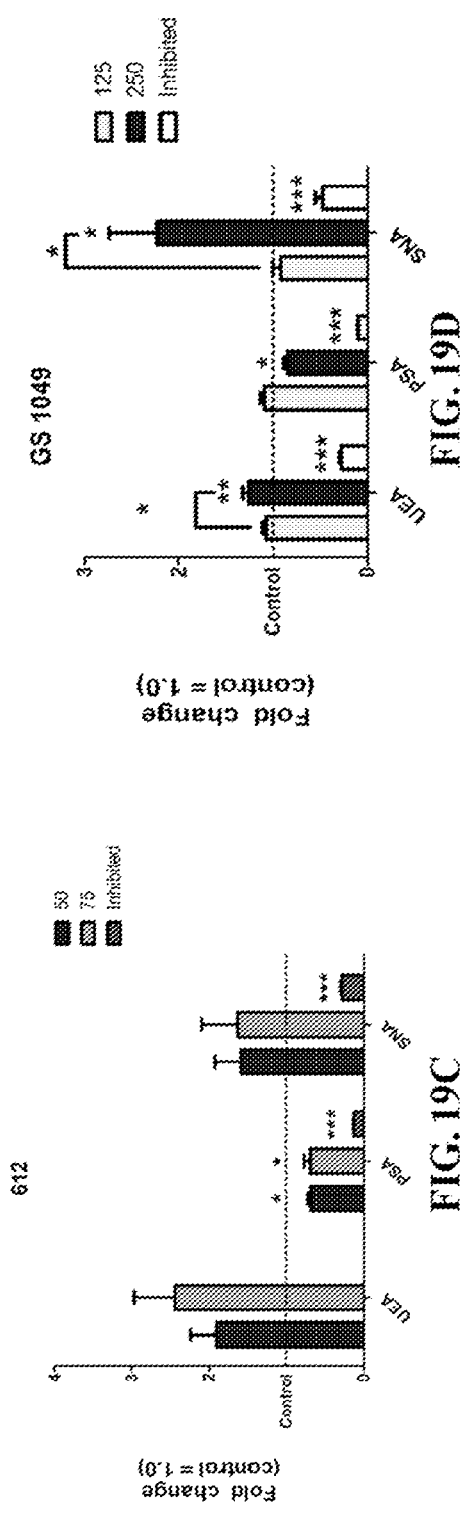
FIG. 19C
FIG. 19D

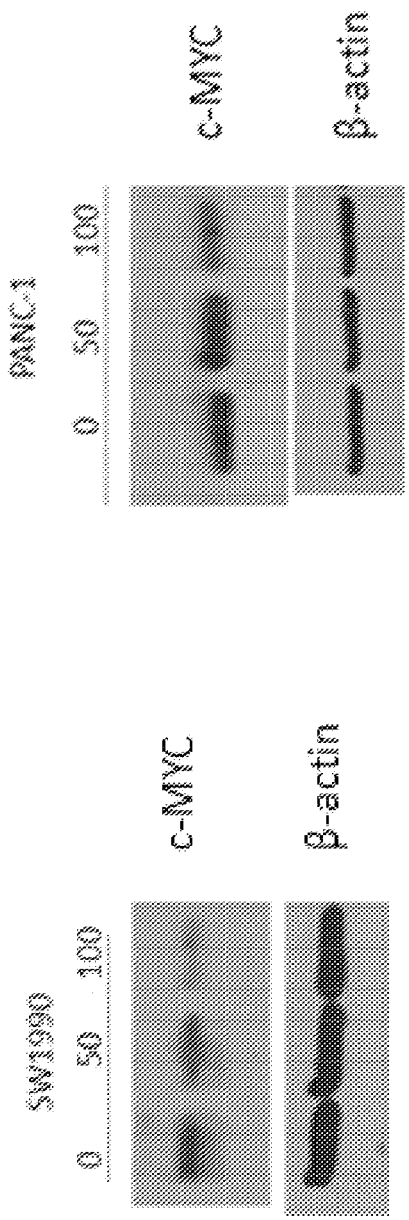
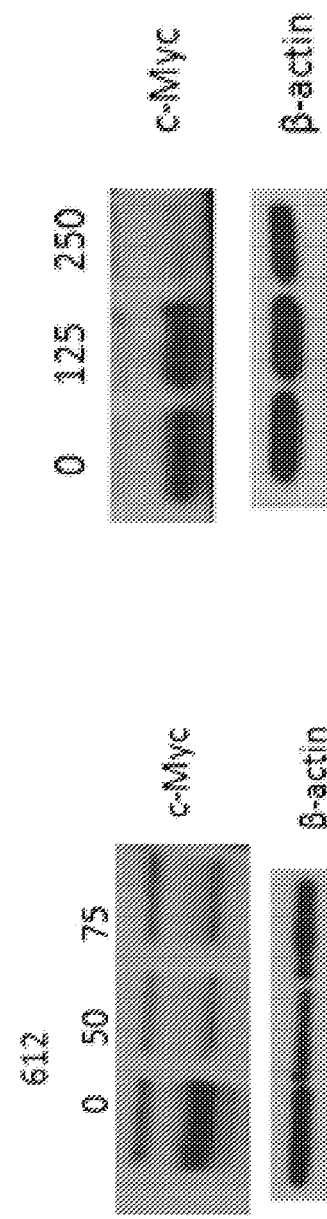
FIG. 21A  FIG. 21B  FIG. 21C  FIG. 21D

USE OF UAP INHIBITORS TO INHIBIT FLUX THROUGH THE HEXOSAMINE BIOSYNTHETIC PATHWAY

CROSS REFERENCE TO RELATED APPLICATION

The present application is a Division of application Ser. No. 15/503,911 filed on Feb. 14, 2017 which is the U.S. national stage pursuant to 35 U.S.C. § 371, of International Application Ser. No. PCT/US2015/045200, filed Aug. 14, 2015 and published in English on Feb. 18, 2016 as publication WO2016/025790 A1, which claims priority to U.S. Provisional Application No. 62/037,745, filed Aug. 15, 2014, entitled, "Use of AGX Inhibitors to Inhibit Flux through the Hexosamine Biosynthetic Pathway", the entire contents of which are incorporated herein for all purposes by this reference.

STATEMENT REGARDING FEDERALLY SPONSORED RESEARCH OR DEVELOPMENT

Research supporting this application was carried out in part under funding from the NIH/NCI (CA112314), NIH/NINDS (NS070024) and the NIH (R21CA191715). The government of the United States has rights in the inventions.

BACKGROUND OF THE INVENTION

Cancer is a disease characterized by abnormal cell growth and/or cell proliferation. Nearly a hundred years ago, cancer cells were first identified to exhibit altered energy/glucose metabolism associated with the abnormal growth of cancer cells. This association is now generally known as the "Warburg effect" (Cell 144, 646-674, (2011)).

As proposed for the Warburg effect (FIG. 1, right), most cancer cells rely upon high glucose uptake and an increased rate of glycolysis for cell proliferation, with such reliance enhanced by several orders of magnitude in cancer cells as compared to a normal cell (Cell Metab 14, 443-451 (2011)). Glucose in the cancer cell, however, is processed through a highly energetically-inefficient pathway that does not involve mitochondira and produces cellular lactate (Biochemische Zeitschrift 152, 319-344 (1924)). In contrast, in a normal cell, glucose is consumed by the more efficient process of mitochondrial glycolysis (FIG. 1, left).

As illustrated in FIG. 2, when glucose is imported from the environs of the cell into the cytosol, glycolysis occurs. Meanwhile, a portion of glucose is processed in the hexosamine biosynthesis pathway (HBP) for glucose utilization such as providing building blocks for glycans, glycoproteins and the like by producing UDP-GlcNAc or UDP-GalNAc. In certain cellular environments like the cancer cell, cancer-promoting glycans are produced. Similarly, aberrant flux through the HBP—and downstream effects on glycan production—is now linked to many additional diseases; the present invention also will provide therapies beyond cancer.

As such, inhibition of highly elevated metabolic flux through the HBP is expected to retard cancer cell proliferation (Science 324, 1029-1033 (2009)) and provide relief in additional disease settings. Various small molecule drug candidates have been developed in vitro and in vivo that attempt to regulate glycolysis flux or its downstream metabolic pathways. However, until now, the enzyme "UAP" (the mammalian counterpart of bacterial "AGX"; discussed in more detail below) has not been effectively targeted for inhibition.

SUMMARY OF THE INVENTION

The present invention relates, at least in part, to compounds and therapeutic uses thereof for treating disease. Particularly, the compounds of the invention may be UAP inhibitors, and certain methods of the invention involve treating disease using UAP inhibitors to suppress or reduce the activity of an abnormal glycolysis pathway.

In one aspect, the present invention provides a compound or pharmaceutically acceptable salt, solvate, anomers or hydrate thereof:

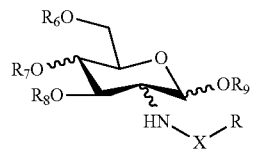

wherein X is CO, $SO_2$ or $CH_2$;
$R_6$, $R_7$, $R_8$, $R_9$, are each independently H or $CO(CH_2)_n CH_3$;
n is 0-16;
R is selected from the group consisting of

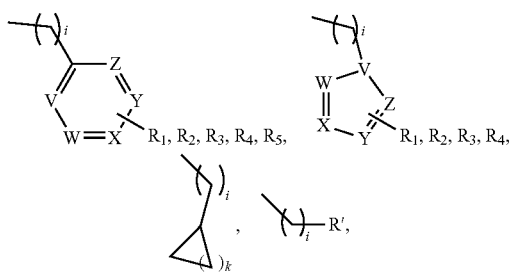

wherein V, W, X, Y, Z are, each independently, C, N, S, or O,
$R_1$, $R_2$, $R_3$, $R_4$, $R_5$ are, each independently, absent, —H, —$(CH_2)_m CH_3$ where m=0-6 including branched alkyls, —Br, —Cl, —F, —I, —$NH_2$, —SH, —$NO_2$, —$NHSO_2 R^a$ where $R^a$ is alkyl or branched alkyl, —$SO_2 NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, R' is substituted or unsubstituted alkyl, which includes heteroatoms NH, O, or S, i is 0 to 16, k is 0 to 10.

In certain embodiments, the compound is selected from the group consisting of:

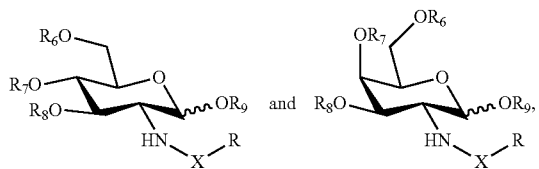

wherein X is CO, SO$_2$ or CH$_2$;

$R_6$, $R_7$, $R_8$, $R_9$, are each independently H or CO(CH$_2$)$_n$CH$_3$;

n is 0-16;

R is selected from the group consisting of

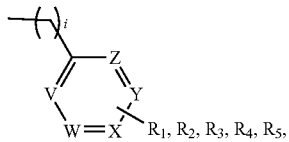 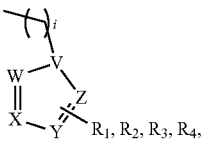

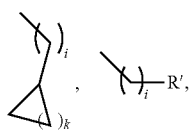

wherein V, W, X, Y, Z are, each independently, C, N, S, or O, $R_1$, $R_2$, $R_3$, $R_4$, $R_5$ are, each independently, absent, —H, —(CH$_2$)$_m$CH$_3$ where m=0-6 including branched alkyls, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, R' is substituted or unsubstituted alkyl, which includes heteroatoms NH, O, or S, i is 0 to 16, k is 0 to 10.

In certain embodiments, X may be CO. Further, $R_6$, $R_7$, $R_8$, $R_9$, may be each independently H or COCH$_3$.

In certain embodiments, R may be selected from the group consisting of

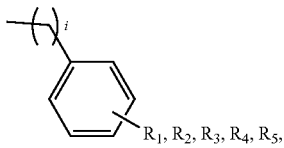

wherein $R_1$, $R_2$, $R_3$, $R_4$, $R_5$ are, each independently, absent, —H, —(CH$_2$)$_m$CH$_3$ where m=0-6 including branched alkyls, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, and i is 0 or 1.

In certain exemplary embodiments, the compound is selected from the group consisting of:

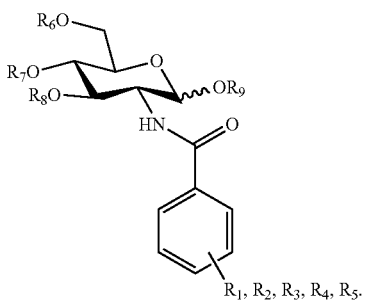

In additional exemplary embodiments, wherein the compound is selected from the group consisting of:

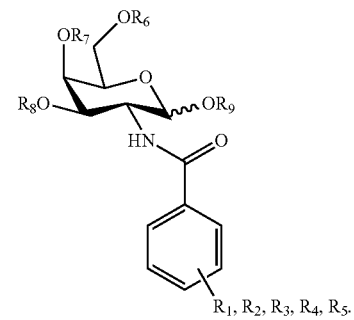

In certain exemplary embodiments, $R_1$ may be OH; and $R_2$, $R_3$, $R_4$ and may be absent.

In an exemplary embodiment, the compound is selected from the group consisting of

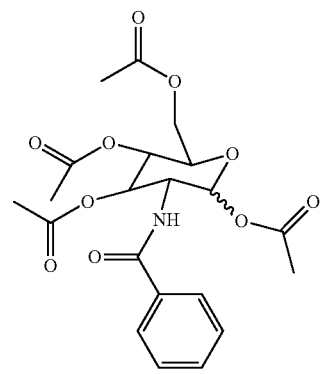

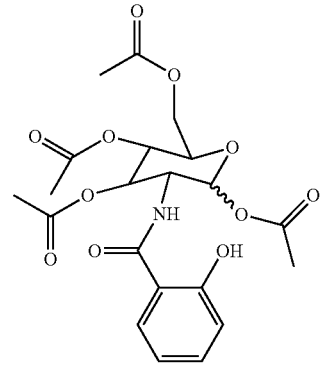

-continued

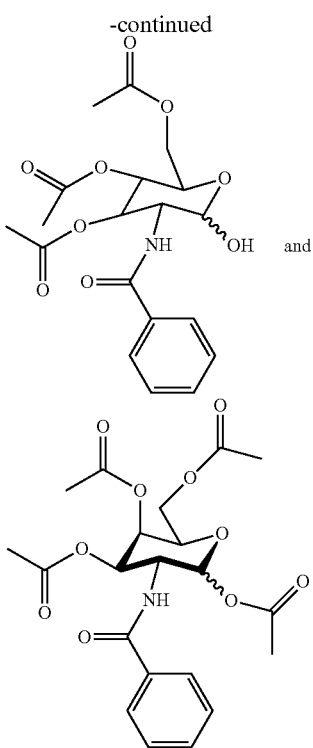

In particular, the compound is a UAP inhibitor.

In one aspect, the present invention also provides a pharmaceutical composition comprising a compound or pharmaceutically acceptable salt, solvate, anomers or hydrate thereof:

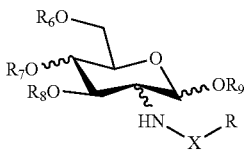

wherein X is CO, SO$_2$ or CH$_2$;
$R_6$, $R_7$, $R_8$, $R_9$, are each independently H or CO(CH$_2$)$_n$CH$_3$;
n is 0-16;
R is selected from the group consisting of

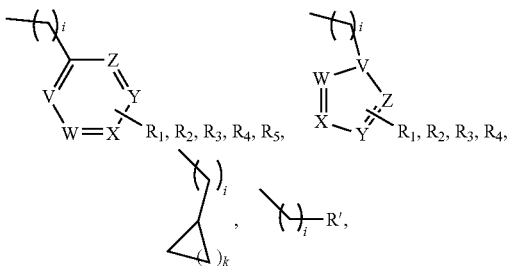

wherein V, W, X, Y, Z are, each independently, C, N, S, or O,
$R_1$, $R_2$, $R_3$, $R_4$, $R_5$ are, each independently, absent, —H, —(CH$_2$)$_m$CH$_3$ where m=0-6 including branched alkyls, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, R' is substituted or unsubstituted alkyl, which includes heteroatoms NH, O, or S, i is 0 to 16, k is 0 to 10, and In certain embodiments, the compound is selected from the group consisting of:

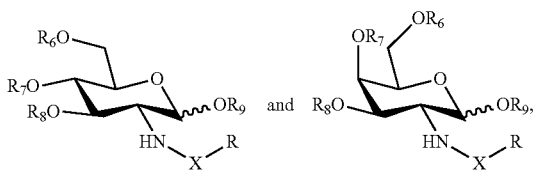

wherein X is CO, SO$_2$ or CH$_2$;
$R_6$, $R_7$, $R_8$, $R_9$, are each independently H or CO(CH$_2$)$_n$CH$_3$;
n is 0-16;
R is selected from the group consisting of

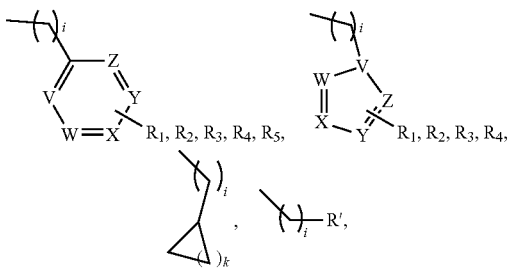

wherein V, W, X, Y, Z are, each independently, C, N, S, or O,
$R_1$, $R_2$, $R_3$, $R_4$, $R_5$ are, each independently, absent, —H, —(CH$_2$)$_m$CH$_3$ where m=0-6 including branched alkyls, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, R' is substituted or unsubstituted alkyl, which includes heteroatoms NH, O, or S, i is 0 to 16, k is 0 to 10.

In certain embodiments, X may be CO. Further, $R_6$, $R_7$, $R_8$, $R_9$, may be each independently H or COCH$_3$.

In certain embodiments, R may be selected from the group consisting of

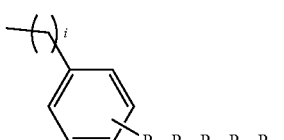

wherein $R_1$, $R_2$, $R_3$, $R_4$, $R_5$ are, each independently, absent, —H, —(CH$_2$)$_m$CH$_3$ where m=0-6 including branched alkyls, —Br, —Cl, —F, —I, —NH$_2$, —SH, —$NO_2$, —$NHSO_2R^a$ where $R^a$ is alkyl or branched alkyl, —$SO_2NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, and i is 0 or 1.

In certain exemplary embodiments, the compound is selected from the group consisting of:

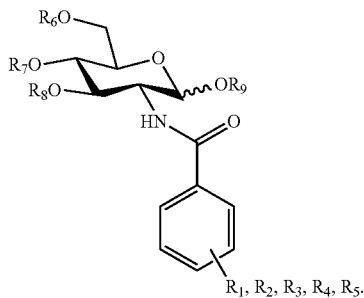

In additional exemplary embodiments, wherein the compound is selected from the group consisting of:

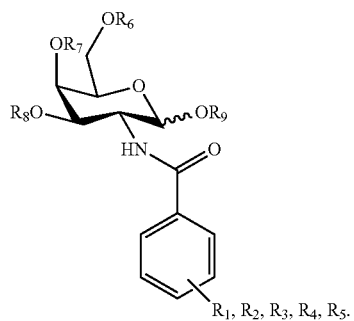

In certain exemplary embodiments, $R_1$ may be OH; and $R_2$, $R_3$, $R_4$ and may be absent.

In an exemplary embodiment, the compound is selected from the group consisting of:

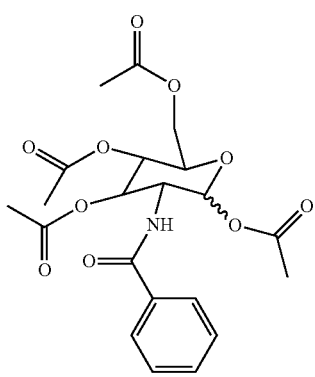

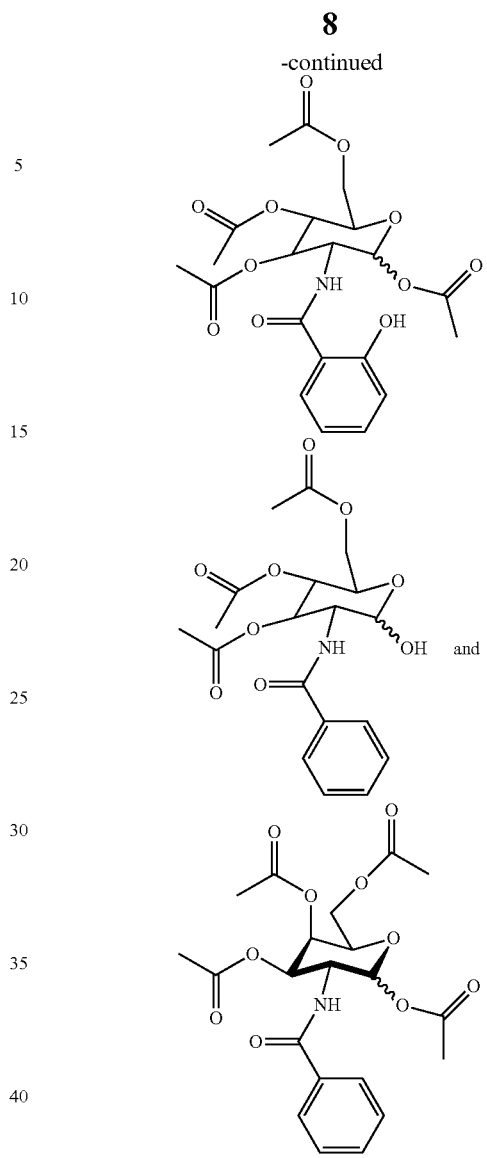

In particular embodiments, the compound is a UAP inhibitor.

In certain embodiments, the pharmaceutical composition may further comprise a bioactive agent in combination with the compound. Further, the pharmaceutical composition may further comprise an anticancer agent in combination with the compound.

Another aspect of the invention provides a method of treating a disease. The method may comprising administering to a subject an effective amount of a pharmaceutical composition comprising the compound of the invention. In particular, the compound of the invention may be a UAP inhibitor.

In certain embodiments, the subject may be an animal or human.

In certain embodiments, the disease may be selected from cancer, diabetes, neurodegenerative disease, metabolic disorder, cardiovascular disease, ageing, autoimmunity, metabolic syndrome, eye disease and kidney disease.

In certain exemplary embodiments, the cancer may be squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas.

In additional exemplary embodiments, the disease may be a metabolic disorder. Exemplary metabolic disorder may be, but not limited to, diabetes or obesity.

In still certain exemplary embodiments, the disease may be a neurological disorder. Exemplary neurological disorder may be an Alzheimer's disease.

In addition, in another aspect, provided is a method of controlling a glycan production in a cell related to a disease. In one embodiment, the method may comprise using the compound of the invention. In particular, the compound of the invention may inhibit UAP activity in hexosamine biosynthesis pathway in the cell.

In certain embodiments, the glycan is a disease-promoting glycan. The disease of the method is described above.

The present invention also provides a kit comprising an applicator, an instructional material for use thereof, and the pharmaceutical composition comprising the compound of the invention.

In certain embodiments, the kit may be used for treating a disease. The disease for the use of kit is described above.

In another aspect, the present invention provides a method for screening a selective inhibitor of UAP. The method may comprise comparing effects of a test compound from a chemical library with effects of the compound of the invention. In particular, the compound of the invention may be a positive control for the screening.

In an exemplary embodiment, the method of screening comprises: treating a first group of subject with the compound; treating a second group of subject with the test compound; and determining a level of the treatment of the test compound based on a level of the treatment of the compound.

In certain exemplary embodiments, the level of treatment may be determined by test results obtained from quantitative cell-free UAP assays, quantitative cell-based UAP assays, quantitative tissue-based UAP assays, cytoxocity assay, cell proliferation assay, qRT-PCR of induced mRNA, knockdown assay, glycosylation profiling, cell adhesion and motility test, drug synergy test or combinations thereof.

Another aspect of the invention provides a method of decreasing YAP/TAZ expression in a mammalian cell, the method involving administering to the mammalian cell a compound of the invention (optionally a UAP inhibitor), where the expression of YAP and/or TAZ is reduced in the mammalian cell by at least 50%, at least 60%, at least 70%, at least 80%, at least 90% or at least 95% or more, as compared to an appropriate control mammalian cell.

An additional aspect of the invention provides a method for suppressing YAP/TAZ activity in a mammalian cell, the method involving administering to the mammalian cell a compound of the invention (optionally a UAP inhibitor), where the activity of YAP and/or TAZ is reduced in the mammalian cell by at least 50%, at least 60%, at least 70%, at least 80%, at least 90% or at least 95% or more, as compared to an appropriate control mammalian cell.

A further aspect of the invention provides a method of treating a brain tumor in a subject involving administering to the subject an effective amount of a pharmaceutical composition of the invention.

Optionally, the brain tumor is a glioma, glioblastoma, meningioma, chordoma, other tumor of the central nervous system, and/or a metastatic tumor to the brain.

Other aspects of the invention are disclosed infra.

BRIEF DESCRIPTION OF THE DRAWINGS

FIG. 4A shows results from exposure to $Ac_4Glc2Bz$, $Ac_4Gal2Bz$, $Ac_4Glc2Bz(2\text{-}OH)$, and 1,3,4-O-$Ac_3Glc2Bz$; and FIG. 4B shows results from exposure to $Ac_4GlcNph$, $Ac_4GalNPh$, $Ac_4GlcNPh(2\text{-}OH)$, and 1,3,4-O-$Ac_3GlcNPh$. In all cases, $IC_{50}$ values were greater than 300 which is the highest concentration tested, for the ACSs, while the $Ac_4Glc2Bz$ analogs and $Ac_4Gal2Bz$ analogs were effective to reduce cell numbers in both cancer cell lines.

FIG. 6B depicts a possible mechanism for this weight gain whereby decreased UDP-GlcNAc via UAP inhibition produces a similar effect observed when OGT is knocked out in mice and significant weight gain is observed due to suppression of AMPK receptor expression resulting from changes in the O-GlcNAc modified states of AMPK receptors.

FIG. 7A depicts the results of primary glioblastoma lines 612 and GS1049 after incubation for 48 h with Ac$_4$Glc2Bz followed by cell counting and normalization to untreated controls. The data is log transformed to easily determine IC$_{50}$ values. FIG. 7B and FIG. 7C depict the measurement of proliferation of the primary glioblastoma lines after 48 h incubation with Ac$_4$Glc2Bz using a MTT assay.

FIG. 16A shows LC-MS/MS traces of UDP-Glc/GalNAc (HexNAc) after treating 612 cells each with 50 µM or 100 µM Ac$_4$Glc2Bz (top); and a reference UDP-GlcNAc (bottom). FIG. 16B shows quantitized LC-MS/MS peaks of UDP-Glc/GalNAc (HexNAc) from FIG. 16A at each of 50 µM and 100 µM Ac$_4$Glc2Bz. (n=3, with error bars representing SEM;* indicates p<0.05)

FIG. 18A shows trace comparisons in N-glycan (low molecular weight) regions between control and Ac$_4$Glc2Bz treatment; and FIG. 18B shows trace comparisons in high MW glycan regions between control and Ac$_4$Glc2Bz treatment.

FIGS. 19A-19D show lectin binding levels in SW1990 (FIG. 19A); Pac-1 (FIG. 19B); 612 (FIG. 19C); and GS1049 cells (FIG. 19D) following treatment with Ac$_4$Glc2Bz. Results were normalized to a control to be 1.0. (n=3 or more; "Inhibited" refers to negative control samples that were treated with competing sugars to inhibit lectin binding; * indicates p<0.05)

FIGS. 21A-21D show that c-MYC expression was altered by Ac$_4$Glc2Bz in a dose-dependent manner in SW1990 (FIG. 21A); PANC-1 (FIG. 21B); 612 (FIG. 21C); and in GS1049 cells (FIG. 21D) when treated either 125 µM or 250 µM Ac$_4$Glc2Bz.

FIG. 22B shows YAP western blot results following shRNA knockdown of UAP1 in PANC-1 cells treated with Ac$_4$Glc2Bz.

DETAILED DESCRIPTION OF THE INVENTION

Figure 1:
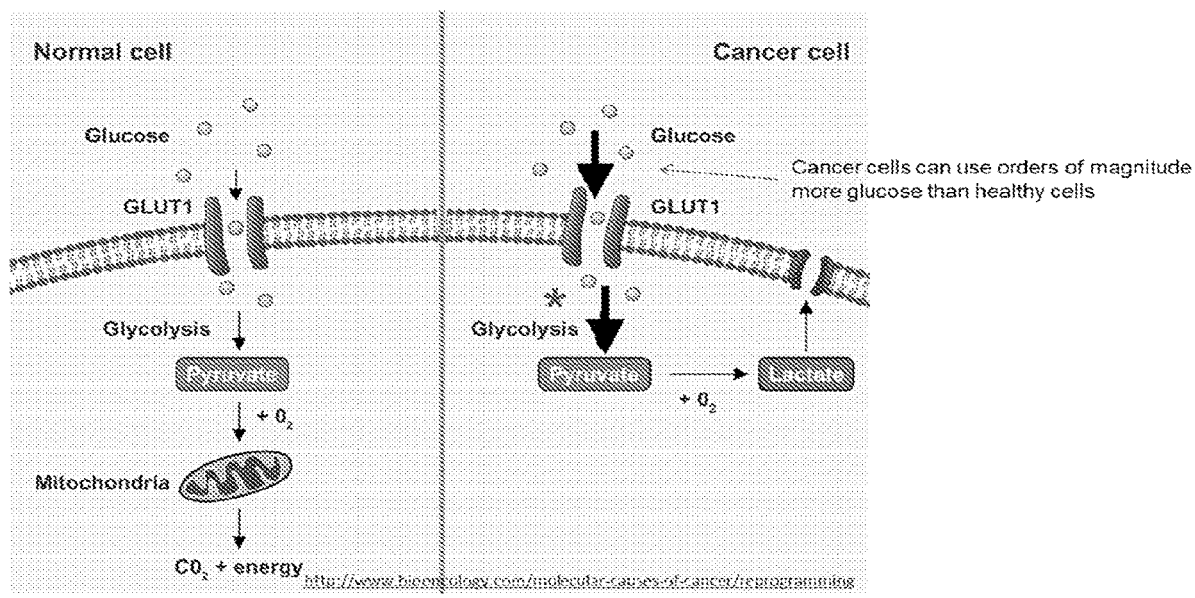
FIG. 1 provides a schematic illustration of abnormally elevated glucose uptake in a cancer cell (right) in comparison to a normal cell (left).

The present invention relates, at least in part, to the discovery that glucose flux through the hexosamine biosynthetic pathway can be regulated or reduced and further that disease-promoting glycan production can be suppressed via use of compounds of the invention. In particular, the compounds of the invention may inhibit UDP-GlcNAc/UDP-GalNAc production, particularly by inhibiting UAP1/2 in the hexosamine biosynthetic pathway. Thus, the present invention is based on evidences that can support the above hypothesis to treat the diseases, such as diabetes and obesity, alzheimer's (Biochimica et Biophysica Acta (BBA)—Molecular Basis of Disease, 1842 (9), 1333-1339 (2014)), which are considered to be associated with aberrantly high glucose flux.

As used here, the term "glycolysis" refers to a metabolic pathway of cellular glucose which is ultimately converted into a pyruvate accompanied with release of high free energy such as ATP or NADPH as an energy source for cellular activity. In certain embodiments, glycolysis and its rate may be altered abnormally, particularly in a cancer cell.

The term "hexosamine biosynthesis pathway (HBP)", as used herein, refers to a metabolic pathway for a sugar to produce cellular hexosamines and derivatives thereof. For example, a portion of about 2-5% of glucose flux into a cellular cytosol is processed by HBP, which results in the production of UDP-N-acetylglucosamine (UDP-GlcNAc) and other nucleotide hexosamines, primarily UDP-N-acetylgalactosamine (UDP-GalNAc). The nucleotide hexoamines so produced may be used for glycosylation of a peptide or producing glycans or glycolipid. In certain embodiments, the HBP may be elevated according to increased glucose uptake in a cancer cell.

The term "glucose flux" as used herein refers to a relative amount of glucose in glycolysis and other glucose cycles such as HBP. In certain embodiments, the glucose flux may be affected by glucose uptake from outside of a cell into a cellular cysotol due to an altered metabolic state of a cell, particularly a cancer cell.

"AGX", as used herein, originally referred to a bacterial gene encoding UDP-N-acetylglucosamine pyrophosphorylase. It should be noted that alternative nomenclature for this enzyme is "UAP", which is the preferred nomenclature in humans, and two isoforms exist in human cells, e.g., AGX1/AGX2 in bacteria or UAP1/2 in mammalian cells (see, e.g., nucleotide sequence NM_003115.4 and corresponding polypeptide sequence NP_003106.3). As such, in certain embodiments, "UAP" encompasses all of these as used herein. UAP is homologous to AGX, which also encodes bacterial UDP-N-acetylglucosamine pyrophosphorylase. Subsequent studies showed that the UAP and AGX gene products or its enzyme convert UTP and GlcNAc-1-P into UDP-GlcNAc and UTP and GalNAc-1-P into UDP-GalNAc. In certain embodiments, as disclosed herein, these enzymes are positioned at a late stage in the HBP (FIG. 2) and inhibited by the compounds of the invention.

The term "downstream" as used herein should be understood as reference to a later stage of an entire metabolic pathway, such as glucose metabolism. In certain embodiments, the downstream portion of a pathway may be regulated or inhibited by a factor, such as a genetic factor or an inhibitor such as a small molecule drug candidate. In an exemplary embodiment, a downstream step of the HBP pathway may be an enzymatic conversion of GlcNAc-1-phosphate into UDP-GlcNAc.

The term "sugar" as used herein should be understood as reference to a monosaccharide which may be used for energy source of a cell or as a building unit for carbohydrates such as glycan. In certain embodiments, the monosaccharide or sugar may be further modified to implement different properties from the unmodified monosaccharide.

The term "hexosamine" as used herein refers to a type of aminosugar, which is generated by adding unsubstituted or substituted amine group on a sugar ring. Exemplary hexosamines include fructosamine, galactosamine, glucosamine, mannosamine, N-acetylated glucose (GlcNAc), N-acetylated galactose (GalNAc), or N-acetylated mannose (ManNAc).

The term "derivatives" or "analog" refer to a compound having a similar structural core and chemical properties to the original compound. The derivatives or analog may be obtained by chemical modifications, such as substitution. In an exemplary embodiment, the compounds in the invention and analogs thereof may include structural similarities to GlcNAc or GalNAc which is a substrate of UAP. Further, the term "2Bz" used as part of the name of hexosamine analog or derivative herein (e.g., "Glc2Bz") refers to a benzamide group (Bz) attached to the 2 carbon of the 2-deoxy sugar ring (e.g., "Glc2Bz" is in essence 2-deoxyglucose with a Bz attached to the 2 position) via the amine group of Bz.

The term "glycan" as used here refers to a type of carbohydrate comprising unmodified or modified monosaccharide units via glycosidic bonds. Glycans may be attached on cellular membrane, proteins, lipids and the like and further modify characteristics of cellular surface. Glycans may be linked to the protein via O-linkage or N-linkage according to the aminoacid side chain to which the glycans make bond. In certain embodiments, the glycans on cancer cell surface may promote metastatic cancer progression or rapid cancer cell proliferation. The building blocks of glycans may be supplied via various sugar metabolism such as hexosamine biosynthesis pathway and Leloir pathway.

By "proliferative disease" or "cancer" as used herein is meant, a disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of disease related gene expression in a cell or tissue, alone or in combination with other therapies.

"Treatment", or "treating" as used herein, is defined as the application or administration of a therapeutic agent (e.g., a compound of the invention) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

Various methodologies of the instant invention include at least one step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing an administration or treatment methodology, as described herein. For example, the activity of a metabolic pathway, the phenotypic or genotypic status of a disease or disorder, etc. can be determined prior to introducing a compound of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

It is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference in their entirety.

Late Stage Inhibition of the Hexosamine Biosynthetic Pathway

In one aspect, the present invention provides a novel method of suppressing or reducing the aberrantly elevated glucose flux in HBP by inhibiting UAP.

Figure 2:
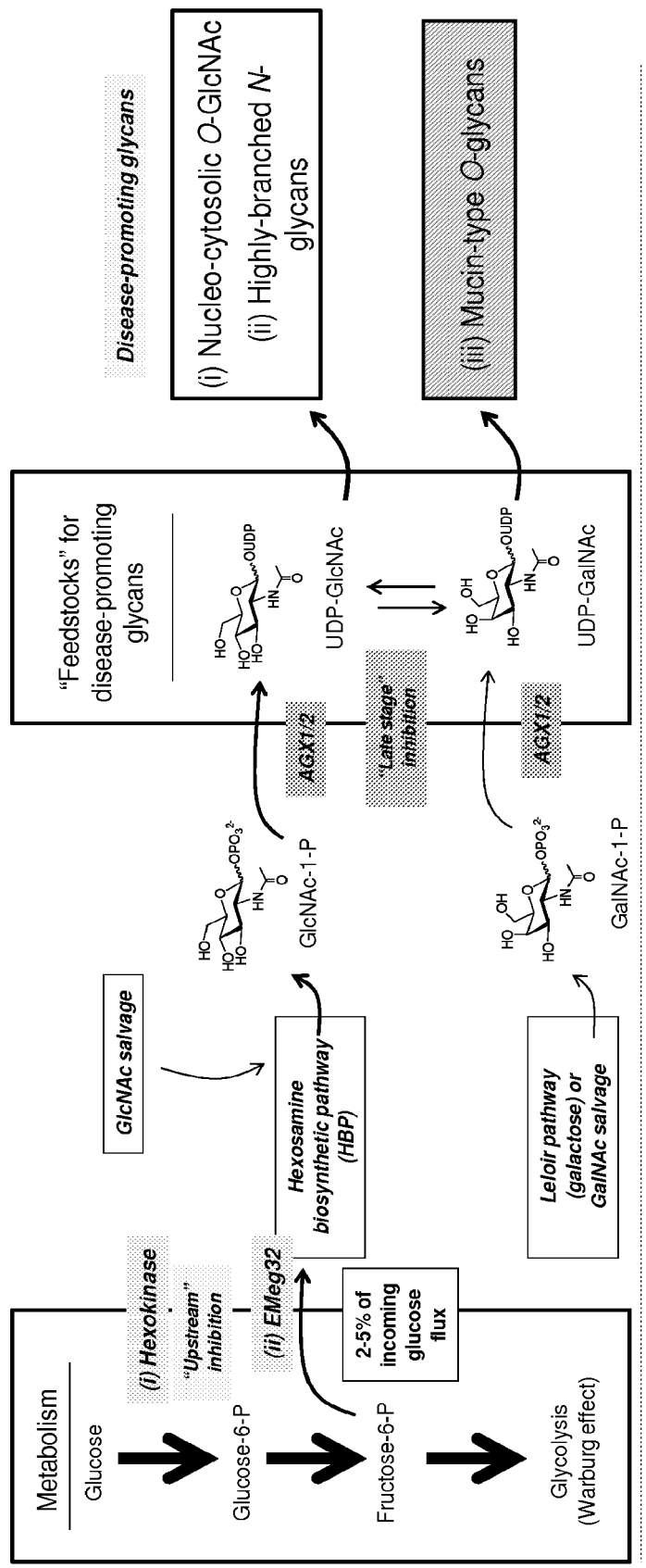
FIG. 2 illustrates links between glucose metabolism and glycosylation. Particularly, in cancer cells, high level of glucose taken into a cellular cytosol is processed in glycolysis pathway as "Warburg effect" (left panel). Further, about 2-5% of glucose flux is engaged in hexosamine biosynthetic pathway (center panel) to produce UDP-GlcNAc (J Biol Chem 284, 24583-24594 (2009)). In addition to glucose-driven flux into HBP, galactose may be engaged as UDP-GalNAc, which is an epimer of UDP-GlcNAc. Those building units are feedstocks for producing cellular glycans, particularly cancer-promoting glycans in the cancer cells as well as for the O-GlcNAc modification. Alternatively, the HBP is also associated with several other complex diseases, such as diabetes and obesity and Alzheimer's. According to the invention, the target enzyme, i.e. UAP (the mammalian counterpart of AGX1/2), for inhibiting HBP is shown in the center panel, marked as "Late Stage Inhibition".

As illustrated in FIG. 2, glucose taken into a cell is subsequently converted into a phosphorylated sugar. Typically about 2 to 5% of incoming glucose flux after this conversion is used in the hexosamine biosynthetic pathway (HBP). In HBP, the UAP, which is known as human UDP-GlcNAc pyrophosphorylase, utilizes phosphorylated GlcNAc, or alternatively phosphorylated GalNAc, to synthesize UDP-GlcNAc or UDP-GalNAc which is incorporated in glycan synthesis or glycosylation. In cancer cells, glycans production increases, and particularly, cancer-promoting glycans in its metastatic is elevated due to supplemental feedstocks of UDP-GlcNAc or UDP-GalNAc in high glucose flux.

Accordingly, the inventive strategy for effective treatment of cancer and other diseases such as diabetes that involve aberrant glucose metabolism includes inhibiting HBP, particularly UAP. This strategy may be referred as "Late Stage Inhibition" because UAP inhibition blocks the very last step of the hexosamine biosynthetic pathway and separates from the downstream glycan production as shown in FIG. 2. This is in contrast to previous efforts to inhibit flux through the hexosamine biosynthetic pathway that targeted "upstream" steps such as hexokinase, GFAT, or EMeg32 (also shown in FIG. 2); a drawback of these previous efforts that the current invention overcomes is that metabolic flux can feed into the hexosamine pathway downstream of these steps, thus thwarting the intended inhibition. By targeting the very last step of the hexosamine biosynthetic pathway, a strategy that has not been reported previously, the current invention is not limited by these drawbacks and may also confer very novel advantages over existing O-GlcNAc transferase inhibitors.

Other diseases which are associated with high flux through the hexosamine biosynthetic pathway represent additional therapeutic targets, through three distinct but overlapping glycosylation-mediated routes with respect to disease outcomes. As shown in FIG. 2, these are (i) intracellular (nucleo-cytosolic)O-GlcNAc protein modification (refs), (ii) increased N-glycan branching (Cell. 24; 139(7): 1229-41, (2009)), and (iii) increased mucin-type O-glycosylation. Exemplary diseases associated with these three types of metabolic flux-driven aberrant glycosylation are disclosed herein: (i) intracellular O-glycosylation has been implicated in cancer (Methods Mol Biol. 1176:73-88 (2014)), diabetes (Proteomics Clin Appl. April; 8(3-4): 218-31 (2014)), neurodegenerative disease exemplified by Alzheimer's disease (Chem Soc Rev. Apr. 24, 2014), metabolic disorder (Trends Endocrinol Metab. June; 24(6):301-9 (2013)), cardiovascular disease (Pharmacol Ther. 142(1):62-71 (2014)), and possibly even ageing (Aging (Albany N.Y.) 2(10):678-90 (2010)); (ii) increased glycan branching has been implicated in many common chronic conditions such as autoimmunity, metabolic syndrome, and aging (Aging (Albany N.Y.) 2(10):678-90 (2010)), as well as cancer (Glycobiology October; 18(10):750-60 (2008)); and (iii) mucin-type O-glycosylation has been implicated most strongly in cancer (Biochim Biophys Acta. 1780(3):546-63 (2008)) but also contributes to eye disease (Curr Opin Allergy Clin Immunol. 8(5):477-83 (2008)), and kidney disease (Semin Nephrol. 24(3):197-217 (2004)). This non-exclusive sampling of diseases linked to abnormal flux through the hexosamine biosynthetic pathway—which can be "normalized" by the current invention with therapeutic applications—illustrates potential applications of the invention.

Benzamide-Derivatized Analogs Inhibiting UAP

As described above, GlcNAc is an enzymatic substrate of UAP. Among derivatives thereof, $Ac_4Glc2Bz$, as shown in Panel B, which is a "druggable" derivative of Glc2Bz (Panel A) has been synthesized and validated as an effective inhibitor of UAP in living cells. Accordingly, in one aspect, structural derivatization based on benzamide-derived hexosamine is provided in the invention.
FIG. 2. Representative AGX/UAP1 inhibitors
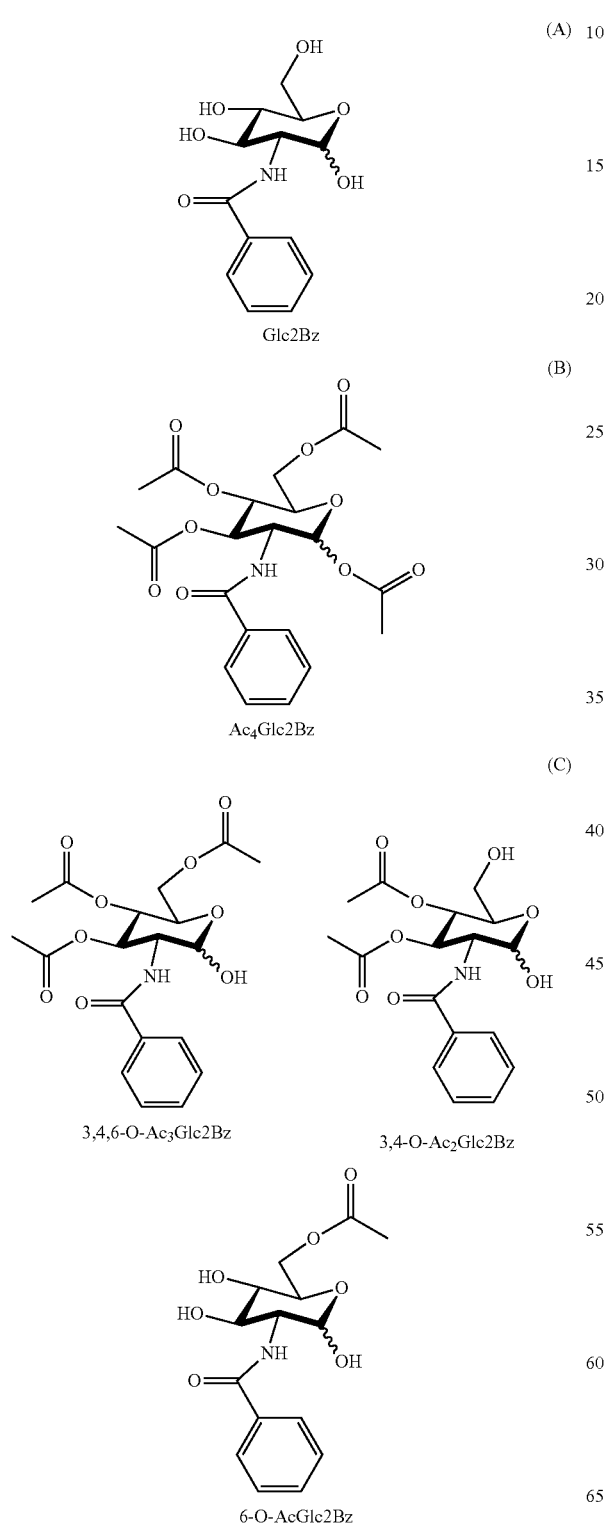
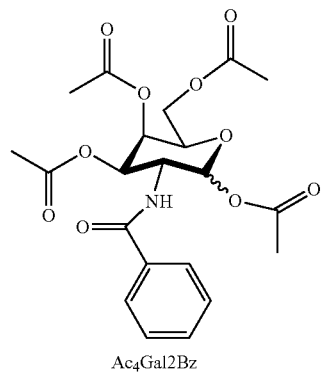
Ac₄Gal2Bz
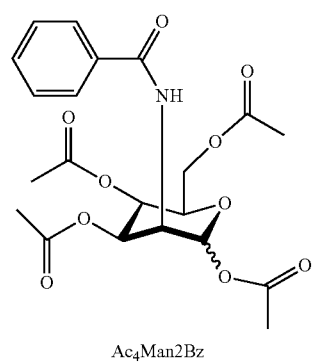
Ac₄Man2Bz

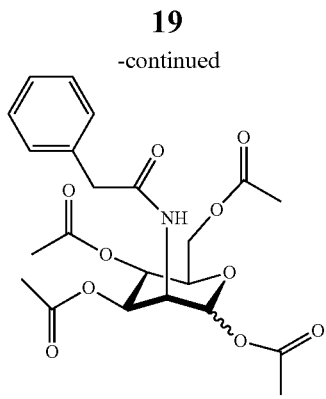

Ac₄ManNAcPh

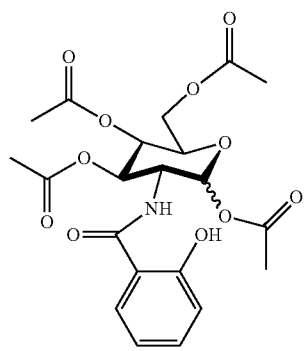

Ac₄Glc2Bz(2-OH)

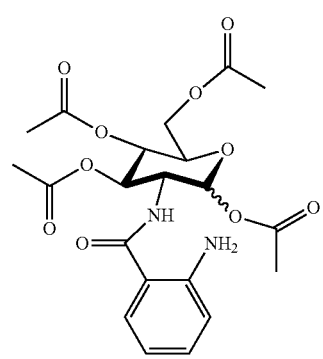

Ac₄Glc2Bz(2-NH₂)

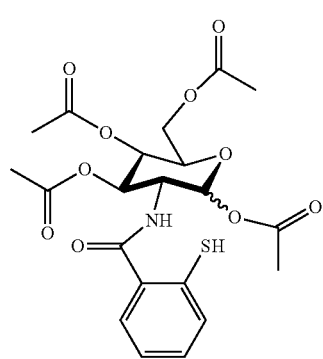

Ac₄Glc2Bz(2-SH)

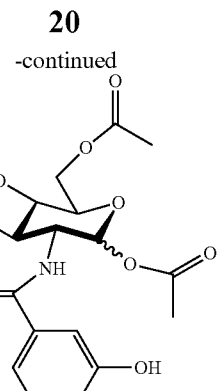

Ac₄Glc2Bz(3-OH)

(F)

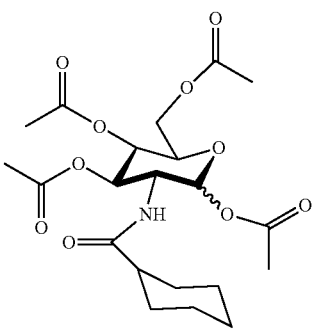

Ac₄GlcNCyx (G)

In (A) to (C) above, exemplary benzamide-derivatized GlcNAc analogs are depicted, and the other derivatives of epimeric N-acetylated hexosamines (GalNAc or ManNAc) are shown in (D) to (G) above.

In certain embodiments, pharmacologically useful prodrugs of Glc2Bz are provided by adding hydrolyzable ester-linked groups. As disclosed herein, the prodrugs refer to compounds capable of being hydrolyzed upon cellular uptake and converted active compounds such as UAP inhibitors.

In additional embodiments, the hydrolyzable ester-linked group may be a short-chain fatty acid (SCFA) group, which preferably includes 2 to 6 carbon atoms but may include longer chains up to 18 carbon atoms, or. Longer or extended chain of SCFA may increase cell permeability of the compounds for cellular intake, but solubility thereof may be reduced in biological or physiological condition. Adding carbon numbers of ester-linked or SCFA may optimize between cell permeability of the compound and other pharmacological properties such as solubility.

In still certain embodiments, a number of the hydrolizable ester-linked group or SCFA may be various upon pharmacological properties thereof. In an exemplary embodiment, 1 to 4 ester-linked group or SCFA may be added on Gal2Bz, Glc2Bz, or Man2Bz analogs. Exemplary compounds which are not fully acetylated are shown in (C) above.

In certain embodiments, compounds may have an extended linker to the benzamide group. The length of the linker may be 0 to 16 atoms, or particularly 0-4 atoms to optimize the pharmacological properties of the compounds. Exemplary compounds which have methylene linkers are shown in (E) above.

In certain embodiments, the electronic and hydrogen bonding properties of the benzamide group may be altered by heteroatomic substitution such as N, S, O and the like.

The compounds with the substitutions on benzamide group may obtain improved affinity or specificity to UAP active site. Alternatively, the compounds with the substitutions may be promoted to have improved pharmacological properties.

In still certain embodiments, the compounds may have other substituent instead of benzamide group on N-acetyl group of hexosamine such as cyclohexane, 5-membered aromatic ring and the like which have structural similarity or chemical properties toward UAP active site.

Compounds have Cancer Cell-Specific Cytotoxicity

The compounds as disclosed herein are proven to have cancer-cell specific cytotoxicity. As previously discovered by the inventors, certain hexosamine analogs may have often but unpredictable mild toxicity and thus such hexoamine analogs may be generally considered to be safe to normal cells.

Figure 3:
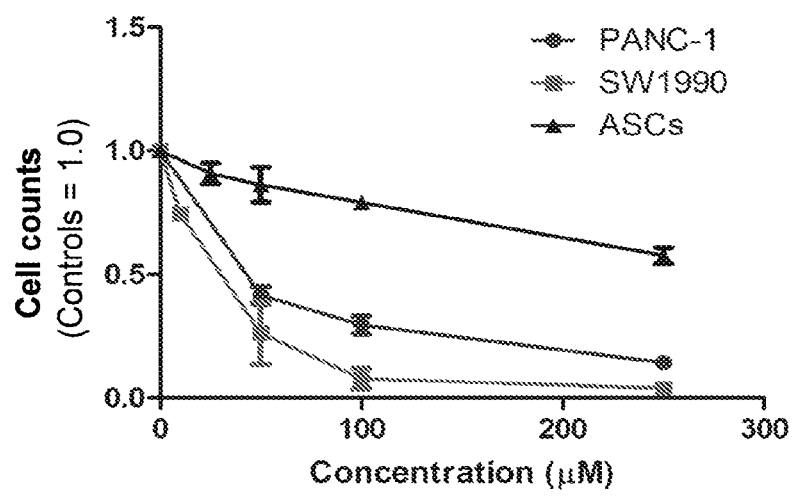
FIG. 3 depicts the result of cell count assays after two days of incubation with an exemplary compound, $Ac_4Glc2Bz$. The cells treated with the compound are, respectively, SW1990 and PANC-1, which are pancreatic cancer cell lines. Meanwhile, control samples were treated with solvent vehicle of 2.5 µL DMSO per 1 mL of medium.

In an exemplary embodiment, the compound Ac$_4$Glc2Bz has a cancer-cell specific cytotoxicity. When cancer cell lines were treated with Ac$_4$Glc2Bz, the cell numbers of treated cancer cell lines reduced. Particularly, when two pancreatic cancer lines (SW1990 and PANC-1 cells) were treated, Ac$_4$Glc2Bz treatment substantially reduced cell numbers with an IC$_{50}$ of about 50 μM, as shown in FIG. 3. Meanwhile, this analog minimally inhibits primary human adipose stem cells (hASCs) which is referenced as normal cells. Accordingly, the Ac$_4$Glc2Bz of the invention has cancer-cell specific toxicity, particularly for the pancreatic and liver cancer cells.

Figure 4A:
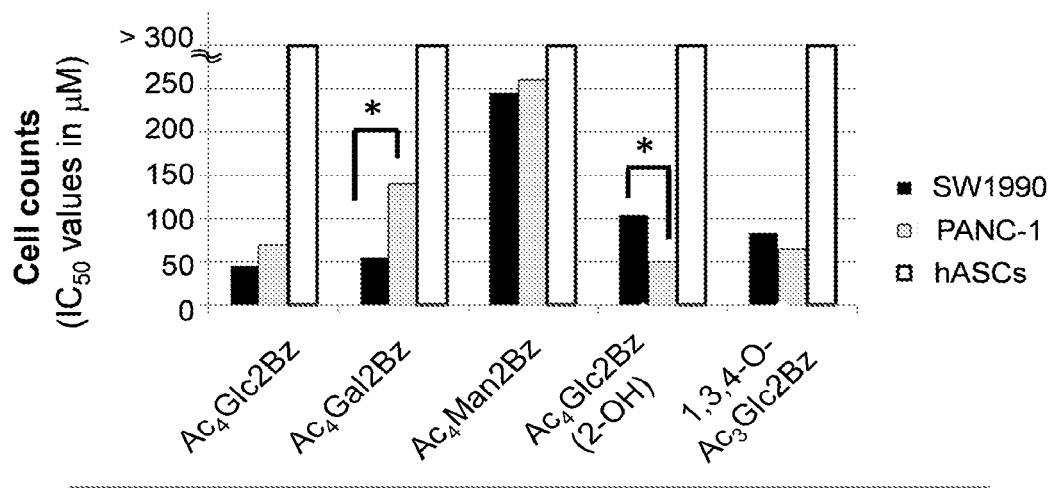
FIG. 4A and FIG. 4B depict histogram results of cell count assays after two days of exposure to each analog in cancer cell lines (SW1990 and PANC-1) and in control cells (human ASCs).
Figure 4B:
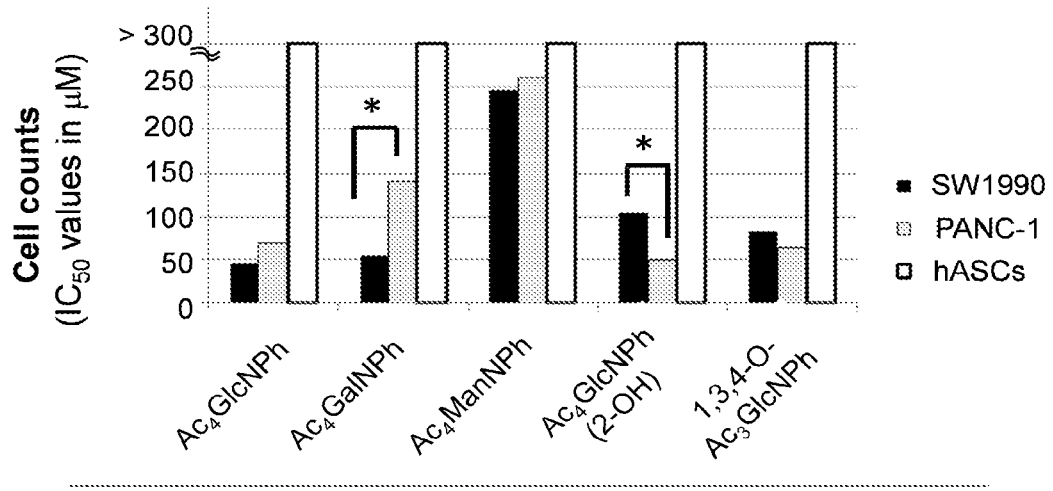

In an expanded cytotoxicity test, other compounds also have cancer-cell specific cytotoxicity. In the cytotoxicity evaluation of the compounds as shown in FIG. 4, certain Glc- and Gal2Bz analogs consistently showed inhibition in the cancer cell lines, while Ac$_4$Man2Bz only had substantially low effect. Particularly, Ac$_4$Glc2Bz(2-OH), 1,3,4-O-Ac$_3$GlcNBz analogs consistently reduced cell numbers in both pancreatic cancer lines, SW1990 and PANC-1 cells. Meanwhile, in all cases, minimal cytotoxicity occurred in the normal ASCs with the treatment of those analogs.

UAP Inhibitors Reduce the Proliferation of Specific Cancer Cells

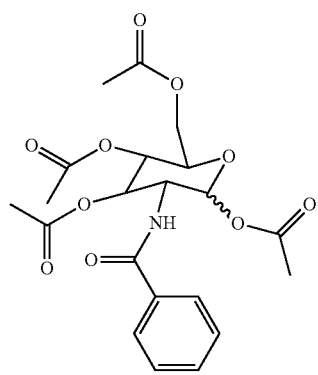

1

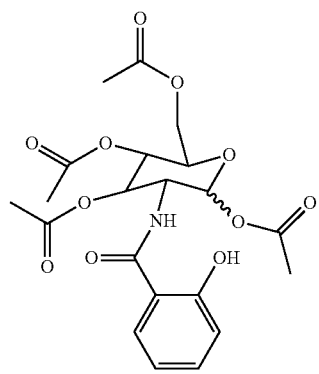

2

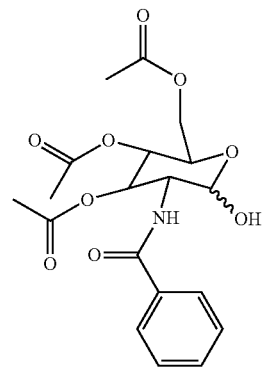

3

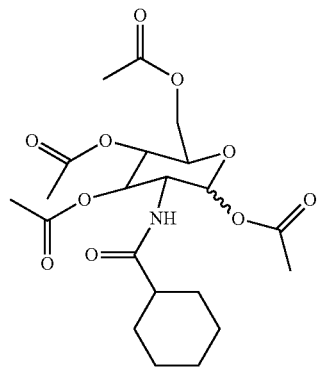

4

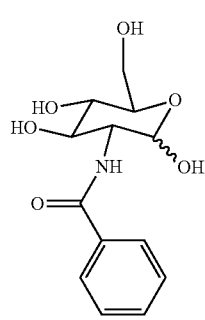

5

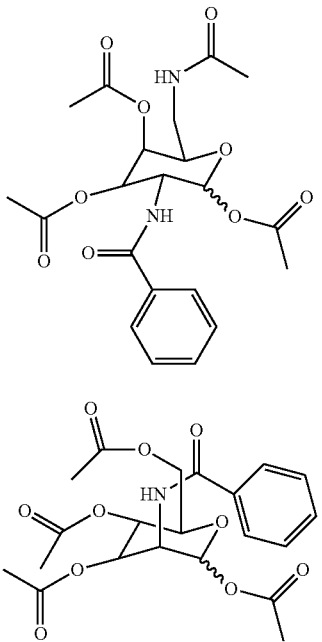

1: Ac₄Glc2Bz  2: Ac₄Glc2Bz-2-OH
3: 3,4,6-O—Ac₃Glc2Bz  4: Ac₄GlcNCyx
5: Glc2Bz  6: Ac₄Gal2NBz
7: Ac₄Man2Bz

Figure 5A:
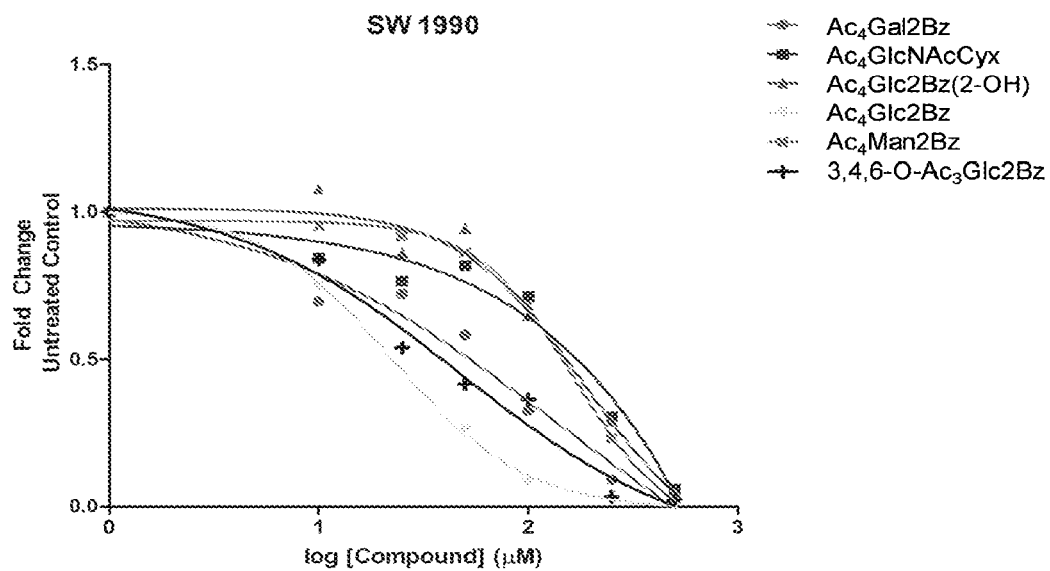
FIGS. 5A and 5B show the results of cell toxicity experiments that were conducted on SW1990 and PANC-1 cells with the analogs indicated. Cells were counted after incubation with each analog for 48 hours. Cell counts were then normalized to controls, data was log transformed, and $IC_{50}$ values were calculated.
Figure 5B:
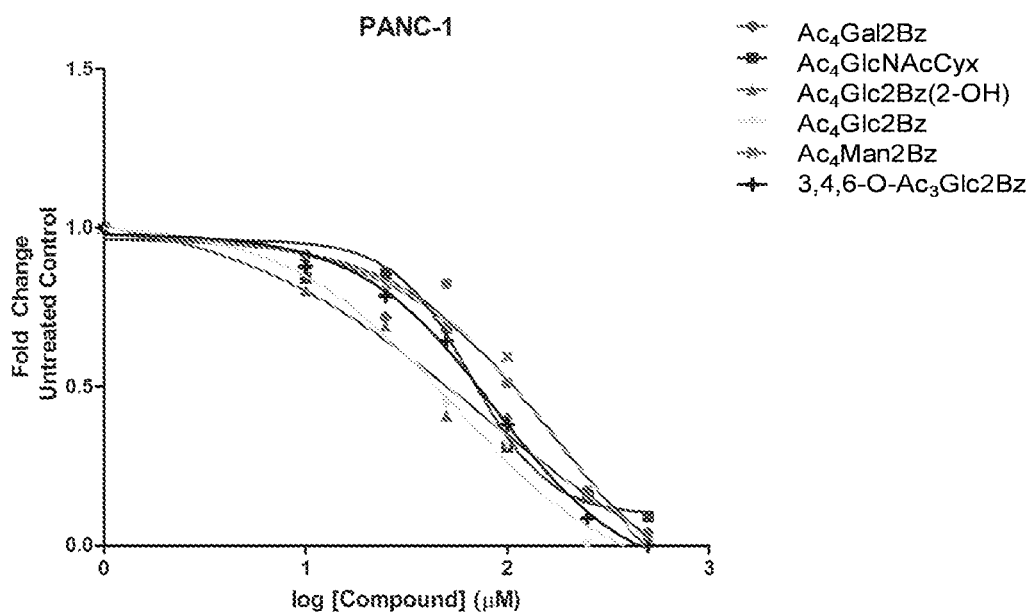

Exemplary compounds of the invention were evaluated with cell proliferation test for specific pancreatic cell lines, SW1990 and PANC-1 cells (FIGS. 5A-5B).

Changes in cancer cell proliferation upon treatments with the compounds on the invention were measured in comparison with the untreated cell lines. As such, SW1990 were treated with effective amounts of the compounds described above and fold change in cell proliferations are shown in FIG. 5A. A several compounds have shown efficacy in suppressing SW1990 cell proliferation at $IC_{50}$ level in a range of from about 25 μM to about 160 μL. Particularly, the lead compound Ac₄Glc2NBz substantially decreases SW1990 cell proliferation at the lowest $IC_{50}$ value. In addition, 3,4,6-Ac₃Glc2Bz and Ac₄Gal2NBz analogs also have remarkable inhibition to SW1990 cell proliferation. In contrast, the other compounds show moderate or less inhibitions or suppressing effects in SW1990, at $IC_{50}$ of about 100 μM or greater.

As shown in FIG. 5B, change in PANC-1 cell proliferation were also evaluated with the compounds of the invention. Similar to the results above, the lead compound Ac₄Glc2NBz substantially decreases PANC-1 cell proliferation at the lowest $IC_{50}$ value of about 45 μL. In this case, Ac₄Glc2NBz-2-OH has similar efficacy in suppressing or inhibiting cell proliferation of PANC-1 pancreatic cell to Ac₄Glc2Bz at $IC_{50}$ value of about 50 μL.

In TABLE I as shown below, summarized are IC50 values of the exemplary compounds of the invention which exhibited efficacy in suppressing cell proliferation in specific cancer cell lines such as PANC-1 and SW1990.

TABLE I

| Compound | Cell line and Estimated IC50 values (μM) | | | |
|---|---|---|---|---|
| | PANC-1 | SW1990 | 612 | GS 1049 |
| Ac₄Glc2NBz | 45.5 ± 1.2 | 25.8 ± 1.5 | 36.2 ± 1.1 | 88.8 ± 1.8 |
| Ac₄Gal2NBz | 107.3 ± 1.1 | 39.1 ± 2.2 | | |
| Ac₄GlcNCyx | 84.1 ± 1.5 | 160.9 ± 1.4 | | |
| Ac₄Glc2NBz-2-OH | 49.9 ± 1.3 | 140.3 ± 1.4 | | |
| Glc2Bz | N.D. | N.D. | | |
| Ac₄Man2Bz | 100.0 ± 1.8 | 147.7 ± 1.5 | | |
| 3,4,6-O—Ac₃Glc2Bz | 76.1 ± 1.6 | 37.1 ± 1.8 | | |

In addition, the lead Ac₄Glc2Bz compound of the invention was effective at inhibiting cell proliferation of other cancer cell lines. Particularly, the compounds of UAP analogs in the invention effectively suppressed cell proliferation of glioblastoma cells including primary 612 line cells and GS1049 cells at an $IC_{50}$ level of about 50 μL.

Further, from those results in TABLE I, structure activity relationships (SAR) exemplified by UAP inhibitor analogs or compounds in the present invention can provide modulated biological activity of the compounds and provide precedent for more widely claiming broad chemical diversity for the analogs.

Safety and Other Implication of UAP Inhibitors

The compounds of the invention as described herein may have little cytotoxicity to normal cells. Further, any noticeable adverse effects are not identified with the compounds of the invention. As such, the compounds are considered to be safe drug candidates when the compounds are used for disease treatment such as cancer treatment.

Figure 6A:
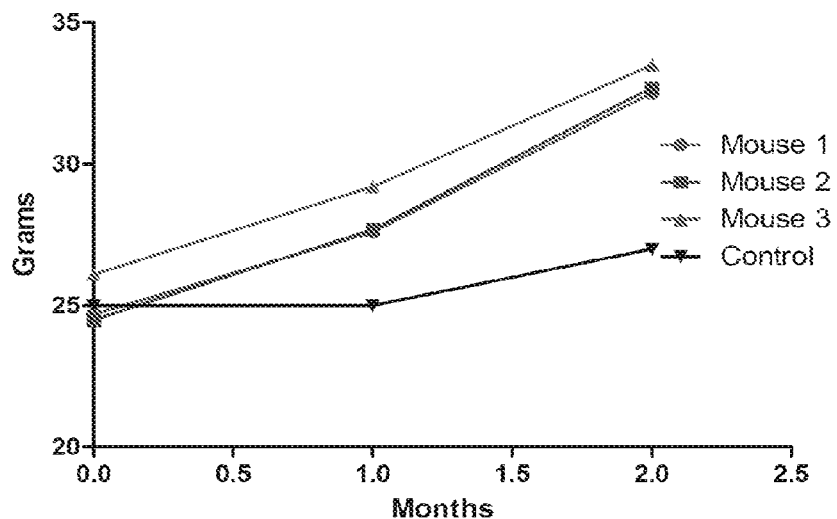
FIGS. 6A and 6B shows results that were obtained from a preliminary in vivo study of $Ac_4Glc2Bz$. Mice were injected (1 mg/kg) with $Ac_4Glc2Bz$ dissolved in DMSO or a DMSO control which were both delivered intraperitoneally. The compound and vehicle were administered for 1 week with dosing intervals every 48 hours. Mice were weighed at the specific time points indicated. Striking weight gain was observed between the three mice treated with Ac$_4$Glc2Bz when compared to the vehicle treated control mouse.
Figure 6B:
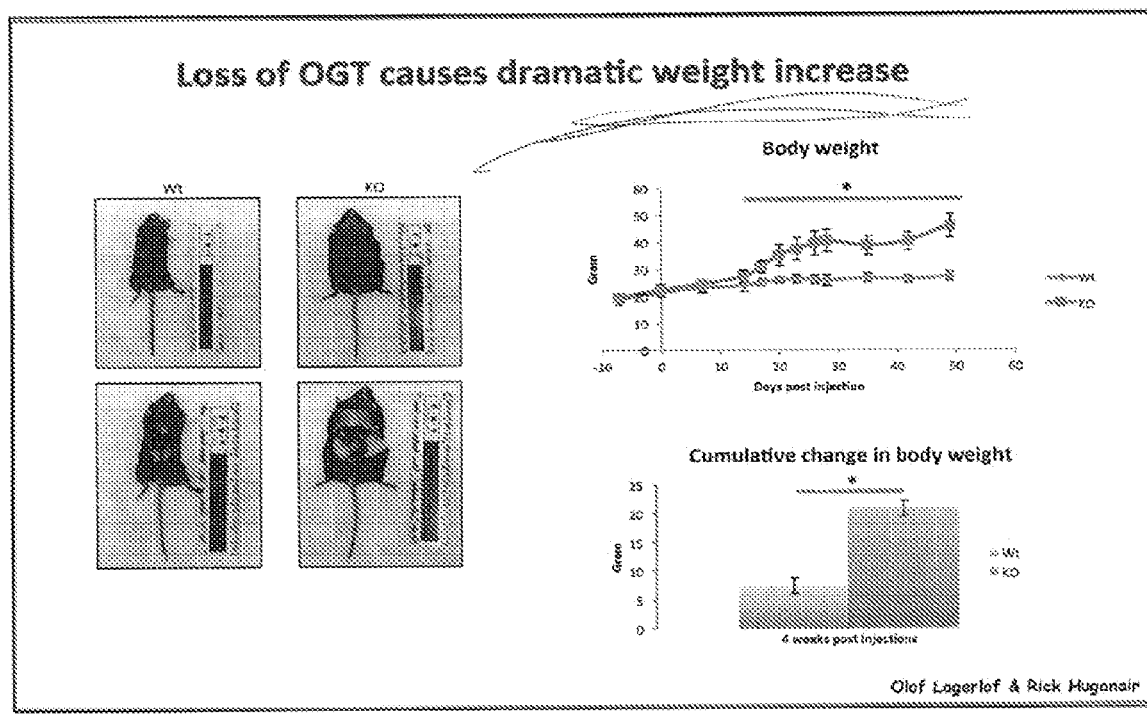
Figure 7A:
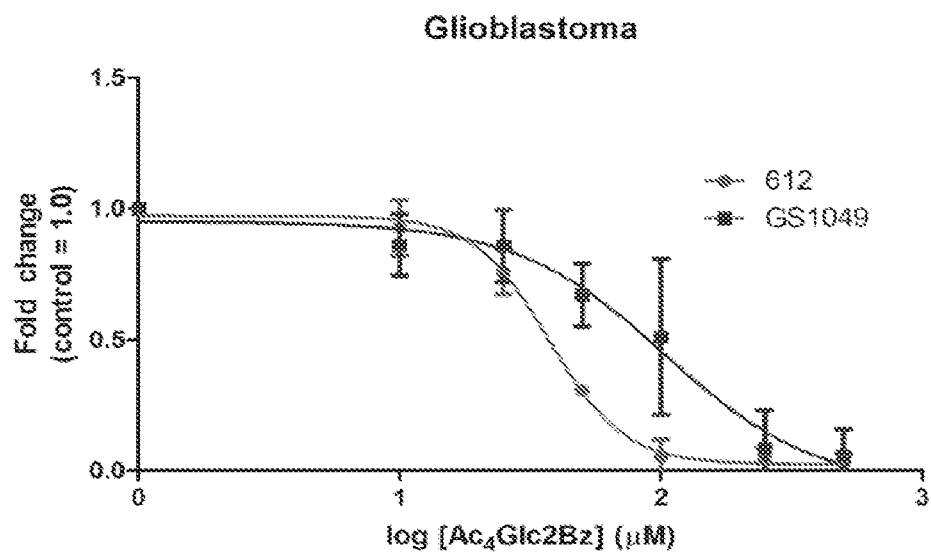
FIG. 7A-7C shows the effects of Ac$_4$Glc2Bz on primary glioblastoma cell lines.
Figure 7B:
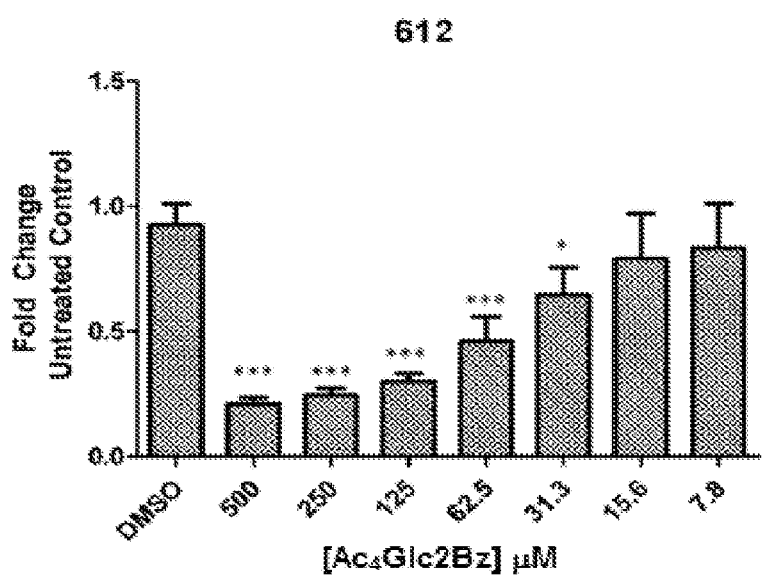
Figure 7C:
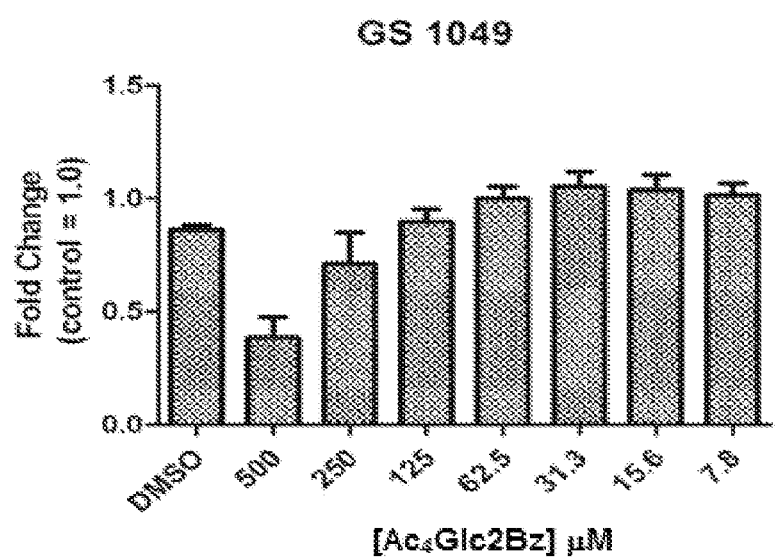
Figure 8:
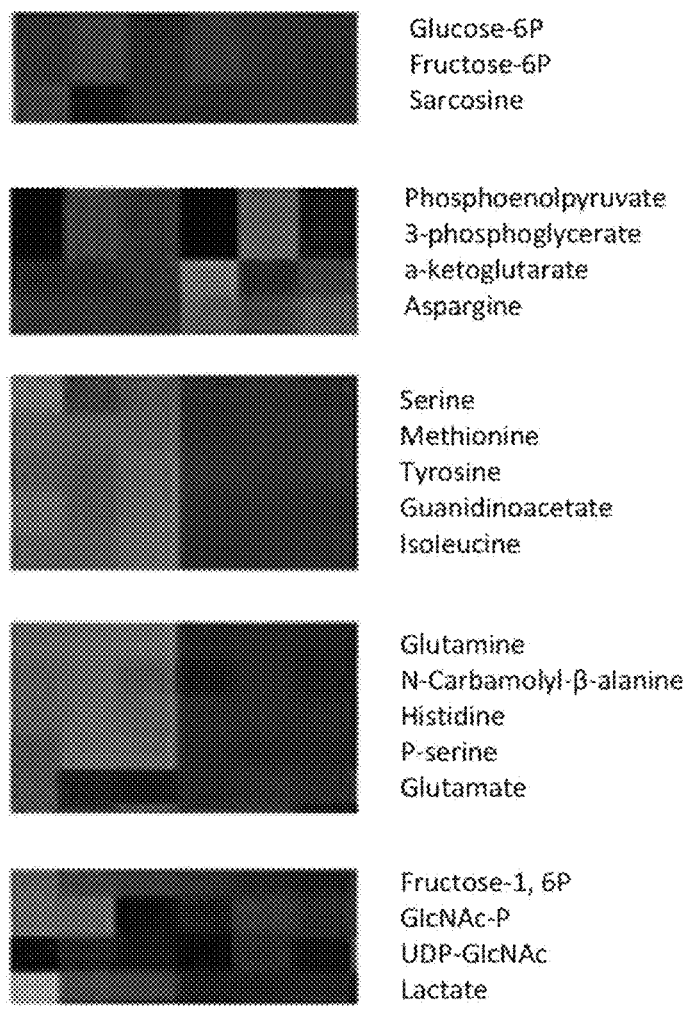
FIG. 8 shows the results from metabolomic studies (Rahman et al. "Targeted metabolomics in cultured cells and tissues by mass spectrometry: Method development and validation", Analytica Chimica Act, in press) performed on cancer cells (HeLa) versus a non-cancerous cell line (Hek293). What was very striking was the fact that the metabolites glucose-6P, fructose-6P, glutamine, fructose-1, 6P, GlcNAc-1P, and UDP-GlcNAc, which are all used by the HBP or products of or within the HBP, appeared to exist at higher quanitites (indicated in shaded form) intracellularly in cancer versus in cells in a non-cancerous state. These studies strongly indicated that i) the Warburg effect was present and ii) that the HBP was overactive in cancer, which provoked the conclusion that a window of selectivity likely existed for HBP inhibition due to increased activity in diseased states.
Figure 9A:
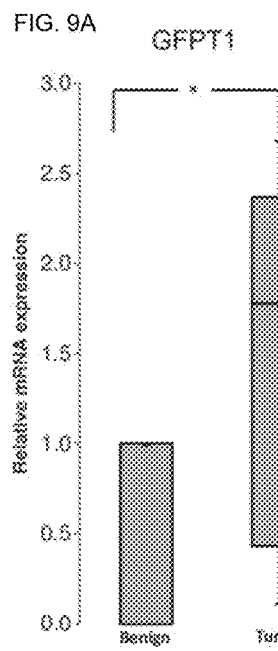
FIG. 9A-9F shows that key enzymes of the HBP machinery, in particular UAP1 (corresponding to bacterial AGX1), were i) overexpressed in prostate tumor tissue vs. benign tissue at both the mRNA and ii) protein level (Cancer Res., 73(16):5277-87, (2013)) in proliferating prostate cancer cells. This study, in conjunction with FIG. 8, strongly supported the idea that diseased cells could be selectively targeted through pharmacological inhibition of UAP1/2 inhibitors over normal cells and tissues due to increased HBP activity and overexpression of HBP enzymes in diseased states.
Figure 9B:
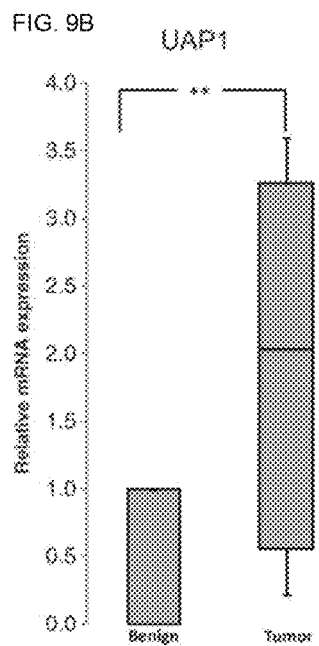
Figure 9C:
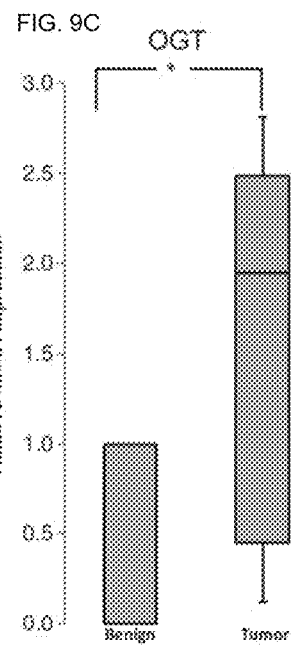
Figure 9D:
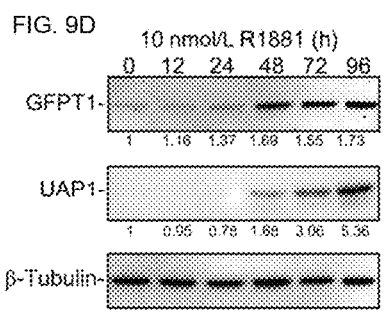
Figure 9E:
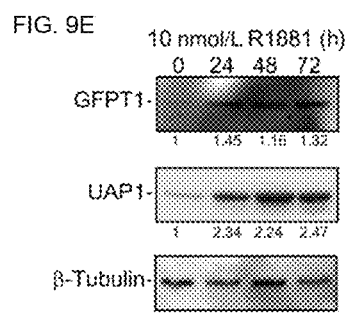
Figure 9F:
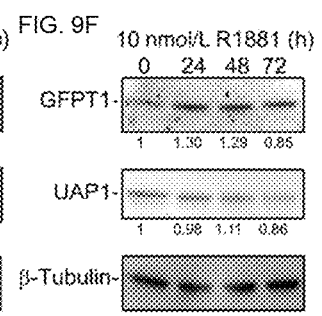

Moreover, when a mouse is treated with the compounds of the invention, the mouse surprisingly gains a weight as shown in FIG. 6A-6B. Furthermore, as suggested by the discovery in the Lagerlof et al., this result may provide further implication that the compounds of the invention may affect AMPA receptors associated in neurological diseases such as Alzheimer's disease.

Effects of UAP Inhibitors on Glycosylation.

UDP-Glc/GalNAc which are synthesized as products of HBP serve as building blocks for glycan biosynthesis and play multiple roles. Accordingly, in one aspect of the present invention, reduced levels of UDP-Glc/GalNAc resulting from UAP inhibition may have effects in reducing production of cellular glycans. Particularly, O-GlcNAc-modified intracellular proteins and highly-branched cell surface N-glycans may be considered as potential target for their regulation.

Normal intracellular concentrations of UDP-Glc/GalNAc may be about 100 μM, and this value is mostly above the $K_m$ of enzymes which use these substrates. Thus, such elevated flux in HBP may barely have impact on the synthesis of most glycans even in cancer cells.

Among those enzymes using UDP-Glc/GalNAc, however, O-GlcNAc modification of intracellular proteins (OGT), which is responsible for O-GlcNAc-modified intracellular proteins synthesis, may depend from various ranges of the UDP-GlcNAc level. For example, the range of UDP-Glc/GalNAc for OGT may fluctuate from the low nM to about 50 mM or greater in vitro assays or from about 0.1 to about 1.0 mM in certain biological conditions.

In addition, MGAT5 which produces highly-branched, tetra-antennary N-glycan structures, has even higher requirements for flux through the HBP, and thus may be active in the presence of 1 to 5 mM UDP-GlcNAc. Based on the Warburg Effect, elevation of glucose flux in the HBP and subsequent increase in UDP-GlcNAc levels in a cancer cell may cause increasing activities of OGT, MGAT5, and the like. Accordingly, the resulting changes in O-GlcNAcylation and the abundance of highly branched N-glycans contribute to developing oncogenesis or metastasis. The present invention, as proposed herein, may provide UAP inhibitors to sequentially de-activate glycan modifying enzymes which are particularly directed to the synthesis of O-GlcNAc-modified intracellular proteins and highly-branched cell surface N-glycans, thereby normalizing glycosylation and suppress disease-promoting glycan synthesis.

SAR can be Used to Target Specific Types of Cells and/or Tissues.

In one aspect of the invention, the structure activity relationships (SAR) from UAP inhibitor such as Glc2Bz may provide further UAP inhibitor candidates, which can be potential drug candidates for treating cancer and the like.

Isoform difference between UDP-N-acetylhexosamine pyrophosphorylases is due to alternate splicing of a single gene which produces an additional 17-amino acid insert near the carboxyl terminus that changes specificity of AGX1 for GalNAc-1-p to GlcNAc-1-p (UAP2) (J Biol Chem. 273(42): 27055-7 (1998)), although the biological significance of this remains controversial (J Biol Chem. 273(42):27055-7 (1998); EMBO J. November 15; 20(22):6191-202 (2001)). Crystal structure characterization of the AGX1 binding domain has established that the N-acetyl arm of the hexosamines forms extensive contact with the enzyme and that certain modifications of the amide arm may be tolerated (ACS Chem. Biol., 7 (4), 753-760 (2012)). Furthermore, there exists a hydrophobic landscape near the amide portion of the sugar consisting of phenyl alanine residues Phe381 and Phe383 (EMBO J., 20(22):6191-202 (2001)). Lastly, while the exact details of UDP-GlcNAc catalysis via UAP remain unclear, there must exist structural rearrangement of the enzyme in order for reactants to enter and products to leave. The crystal structure and sequencing studies performed on AGX/UAP provide an impetus for rational SAR design of a potential UAP inhibitor, whereby hydrophobic amide substitutions can be made to exploit the hydrophobic landscape near the amide arm. Additionally, consideration of the electronic nature of Phe381 and Phe383 in the hydrophobic portion of AGX suggest that phenyl substituted amides on GlcNAc or GalNAc scaffolds could interact quite well with these amino acid residues due to aromatic-aromatic interactions. Phenyl substitution may theoretically provide inhibition of AGX/UAP activity through prohibition of the structural rearrangement that is likely needed for reactants to enter AGX/UAP and the products of catalysis to leave and some circumstantial evidence has suggested this may be the case (Chemistry; 16(45):13343-5 (2010)).

As disclosed herein, $Ac_4Glc2Bz$ and $Ac_4Gal2Bz$ are first in class inhibitors of UAP through rationally designed SAR. By exploiting the scaffold differences between GlcNAc and GalNAc, each isoform of UAP analogs with increased specificity are disclosed. Changing the electronic properties of the amide portion of the analogs as shown in the toxicity studies that compare $Ac_4Glc2Bz$ to $Ac_4GlcCyx$ and $Ac_4Glc2Bz$-2-OH also provides an additional layer of SAR information that can be used to tune potency of the compounds. The consequences of such established SAR are quite profound in that it provides a method through which specific tissues and cells may be able to be targeted through choice of inhibitor being used. For example, a disease or tissue most characterized by aberrations in mucin type glycosylations or tissues that overexpress UAP1 may benefit more from use of $Ac_4Gal2Bz$ and related analogs on the GalNAc scaffold while O-GlcNAc cycling events, N-linked glycosylation, and tissues that overexpress UAP2 may be most appropriately be targeted with $Ac_4Glc2Bz$ and related analogs. Through rational design based on emerging SAR, the desired biological function of UAP1/2 inhibitors may be modified depending on the application. Combination of both types of UAP inhibitors may also produce a profound therapeutic benefit through global reprogramming of virtually every type of major glycosylation event stemming from altered carbohydrate metabolism in the related diseases.

Analogs for UAP Inhibitor

Accordingly, the compounds as a UAP inhibitor in the present invention are provided.

In one aspect, the present invention provides hexosamine analogs for inhibiting UAP. Particularly, GalNAc or GlcNAc analogs are disclosed as candidates for UAP inhibitors. Meanwhile, ManNAc, which is a hexosamine epimer of GalNAc or GlcNAc, and analogs thereof may be also provided as candidates for UAP inhibitor.

In an exemplary embodiment, the compound for UAP inhibitor may be represented as compounds below.

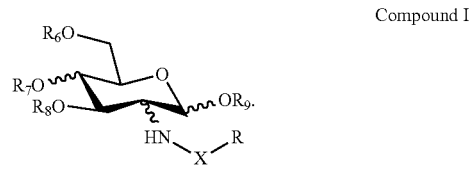

Compound I

Exemplary compounds of the Compound I may be, but not limited to, GlcNAc analogs, GalNAc analogs, and ManNAc analogs.

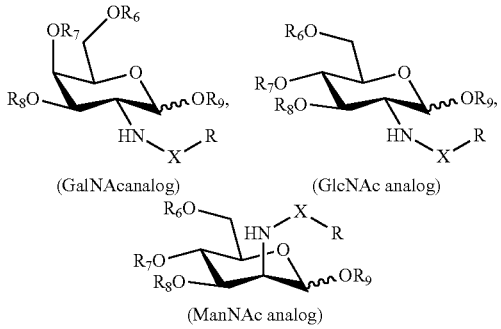

(GalNAc analog)  (GlcNAc analog)

(ManNAc analog)

In certain exemplary embodiments, the compound for UAP inhibitor may be selected from the group consisting of:

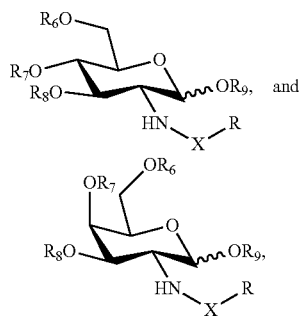

and wherein X is CO, $SO_2$, or $CH_2$;

$R_6$, $R_7$, $R_8$, $R_9$, are each independently H or $CO(CH_2)_n CH_3$;

n is 0-16;

R is selected from the group consisting of

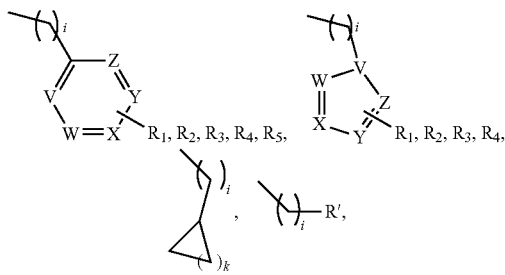

wherein V, W, X, Y, Z are, each independently, C, N, S, or O, $R_1$, $R_2$, $R_3$, $R_4$, $R_5$ are, each independently, —H, —$(CH_2)_m CH_3$ where m=0-6 including branched alkyls, —Br, —Cl, —F, —I, —$NH_2$, —SH, —$NO_2$, —$NHSO_2R^a$ where $R^a$ is alkyl or branched alkyl, —$SO_2NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, R' is substituted or unsubstituted alkyl, which includes heteroatoms NH, O, or S, i is 0 to 16, k is 0 to 10.

In certain embodiments, X is CO.

In additional embodiments, $R_6$, $R_7$, $R_8$, $R_9$, are each independently H or $COCH_3$.

In certain exemplary embodiments, the compound may be α-anomer, β-anomer or combinations thereof, without limitation. Simultaneous and reversible anomerization may occur to form a stable compound in biological condition or physiological condition.

In certain embodiments, R is selected from the group consisting of

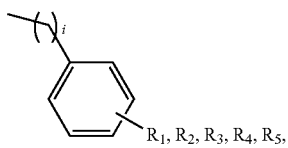

wherein $R_1$, $R_2$, $R_3$, $R_4$, $R_5$ are, each independently, absent, —H, —$(CH_2)_m CH_3$ where m=0-6 including branched alkyls, —Br, —Cl, —F, —I, —$NH_2$, —SH, —$NO_2$, —$NHSO_2R^a$ where $R^a$ is alkyl or branched alkyl, —$SO_2NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, and i is 0 or 1.

In certain exemplary embodiments, i is 0.

In an exemplary embodiment, the compound may be selected from the group consisting of:

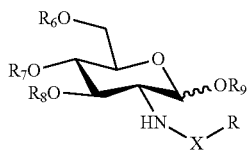

wherein X is CO, $R_6$, $R_7$, $R_8$, $R_9$, are each independently H or $CO(CH_2)_n CH_3$, where n is 0-6; and the other groups are as described above.

In an exemplary embodiment, the compound may be selected from the group consisting of:

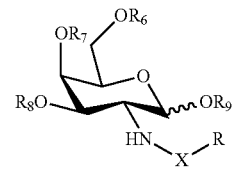

wherein X is CO, $R_6$, $R_7$, $R_8$, $R_9$, are each independently H or $CO(CH_2)_n CH_3$, where n is 0-6; and the other groups are described above.

In certain exemplary embodiments, wherein $R_1$ is OH; and $R_2$, $R_3$, $R_4$ and $R_5$ are absent.

In certain exemplary embodiments, the compound may be

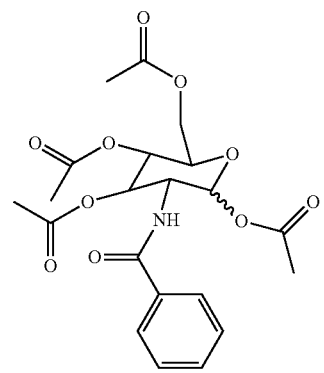

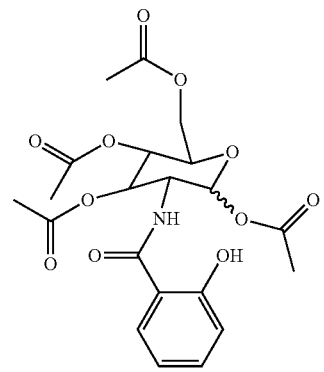

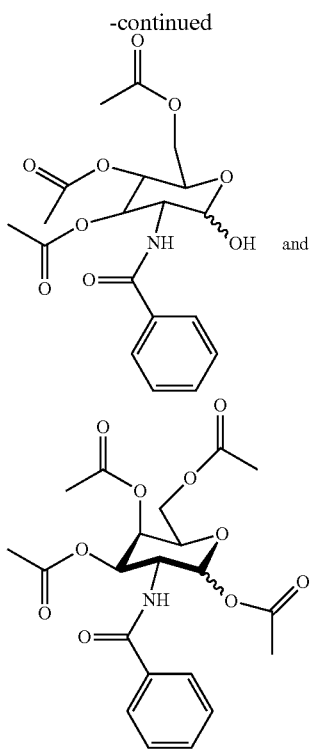

In another aspect, the present invention provides UAP inhibitor analogs which may be derived from non-natural or modified hexosamine.

Compounds

The compounds of the invention are designed to have late stage, downstream inhibition that normalizes the effects of disease-associated glucose-driven flux through the hexosamine biosynthetic pathway, particularly by inhibiting UAP.

As used herein, the term "alkyl" refers to a straight-chained or branched hydrocarbon group containing 1 to 18 (e.g., C1-C-18, inclusive; and any sub-range thereof) carbon atoms. The term "lower alkyl" refers to a C1-C6 alkyl chain. Examples of alkyl groups include methyl, ethyl, n-propyl, isopropyl, n-butyl, sec-butyl, tert-butyl, pentyl (n-, sec-, tert-), and pivaloyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent group. The term "ester" refers to a —C(O)O—R, wherein R is as defined herein. An "amido" is an —C(O)NH$_2$, and an "N-alkyl-substituted amido" is of the formula C(O)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cycloalkenyl" refers to a hydrocarbon 3-8 membered monocyclic or 7-14 membered bicyclic ring system having at least one non-aromatic ring, wherein the non-aromatic ring has some degree of unsaturation. Cycloalkenyl groups may be optionally substituted with one or more substituents. In one embodiment, 0, 1, 2, 3, or 4 atoms of each ring of a cycloalkenyl group may be substituted by a substituent. Examples of cycloalkenyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "arylalkyl" means an aryl group that is attached to another group by a ($C_1$-$C_6$)alkylene group. Arylalkyl groups may be optionally substituted, either on the aryl portion of the arylalkyl group or on the alkylene portion of the arylalkyl group, with one or more substituent. Representative arylalkyl groups include benzyl, 2-phenyl-ethyl, naphth-3-yl-methyl and the like.

As used herein, the term "alkylene" refers to an alkyl group that has two points of attachment. The term "($C_1$-$C_6$) alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH (CH$_3$)—), and the like.

The term "arylalkoxy" refers to an alkoxy substituted with aryl.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkane or alkene. Heteroarylalkyl groups may be optionally substituted, either on the heteroaryl portion of the heteroaralkyl group or on the alkyl portion of the heteroarylalkyl group, with one or more substituents. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocycloalkenyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include 2-pyrrolinyl, 3-pyrrolinyl, 4H-pyranyl, 2-pyrazolinyl, dihydrofuranyl, dihydrothiophenyl, 2-imidazolinyl, indolinyl and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR), wherein R is as defined herein.

In other embodiments, substituents on any group (such as, for example, alkyl, alkenyl, alkynyl, aryl, arylalkyl, heteroaryl, heteroaralkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, aryl sulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, aryl sulfonyl amino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})$ NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocyclyl, or heteroaryl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, crémes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucuronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, oxalic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

Pharmaceutical Composition

In one aspect, the present invention provides a pharmaceutical composition which can be administered in an effective amount thereof. As used herein, the term "composition" or "pharmaceutical composition" refers to a mixture of at least one compound useful within the invention with a pharmaceutically acceptable carrier. The pharmaceutical composition facilitates administration of the compound to a subject.

In one embodiment, the pharmaceutical composition of the invention comprises a compound selected from the group consisting of:

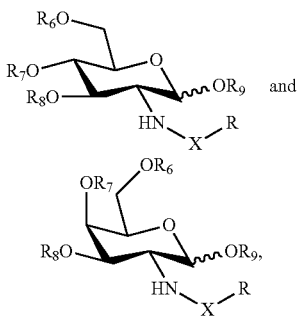

wherein X is CO, $SO_2$, or $CH_2$;

$R_6$, $R_7$, $R_8$, $R_9$, are each independently H or $CO(CH_2)_n CH_3$;

n is 0-16;

R is selected from the group consisting of

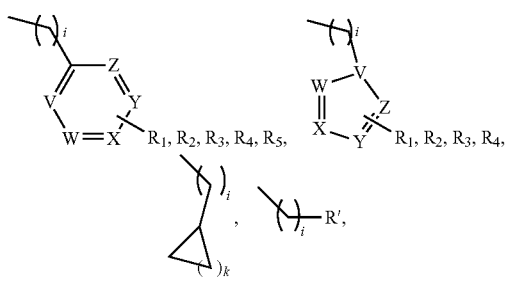

wherein V, W, X, Y, Z are, each independently, C, N, S, or O, $R_1$, $R_2$, $R_3$, $R_4$, $R_5$ are, each independently, —H, —$(CH_2)_m$ $CH_3$ where m=0-6 including branched alkyls, —Br, —Cl, —F, —I, —$NH_2$, —SH, —$NO_2$, —$NHSO_2R^a$ where $R^a$ is alkyl or branched alkyl, —$SO_2NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, R' is substituted or unsubstituted alkyl, which includes heteroatoms NH, O, or S, i is 0 to 16, k is 0 to 10.

In certain embodiments, X is CO.

In additional embodiments, $R_6$, $R_7$, $R_8$, $R_9$, are each independently H or $COCH_3$.

In certain exemplary embodiments, the compound may be α-anomer, β-anomer or combinations thereof, without limitation. In certain embodiments, R is selected from the group consisting of

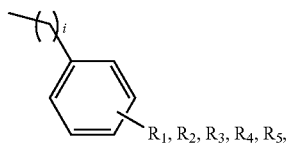

wherein $R_1$, $R_2$, $R_3$, $R_4$, $R_5$ are, each independently, absent, —H, —$(CH_2)_m CH_3$ where m=0-6 including branched alkyls, —Br, —Cl, —F, —I, —$NH_2$, —SH, —$NO_2$, —$NHSO_2R^a$ where $R^a$ is alkyl or branched alkyl, —$SO_2NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, and i is 0 or 1.

In certain exemplary embodiments, i is 0.

In an exemplary embodiment, the compound of the pharmaceutical composition of the invention may be selected from the group consisting of:

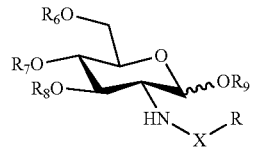

wherein X is CO, $R_6$, $R_7$, $R_8$, $R_9$, are each independently H or $CO(CH_2)_n CH_3$, where n is 0-6; and the other groups are described above.

In an exemplary embodiment, the compound for methods of treating the disease may be selected from the group consisting of:

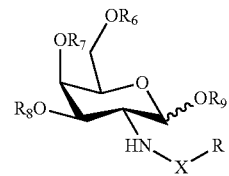

wherein X is CO, $R_6$, $R_7$, $R_8$, $R_9$, are each independently H or $CO(CH_2)_n CH_3$, where n is 0-6; and the other groups are described above.

In certain embodiments, and R is unsubstituted or substituted phenyl group.

In additional embodiments, $R_6$, $R_7$, $R_8$, $R_9$, are each independently H or $COCH_3$.

In an exemplary embodiment, the compound may be selected from the group consisting of:

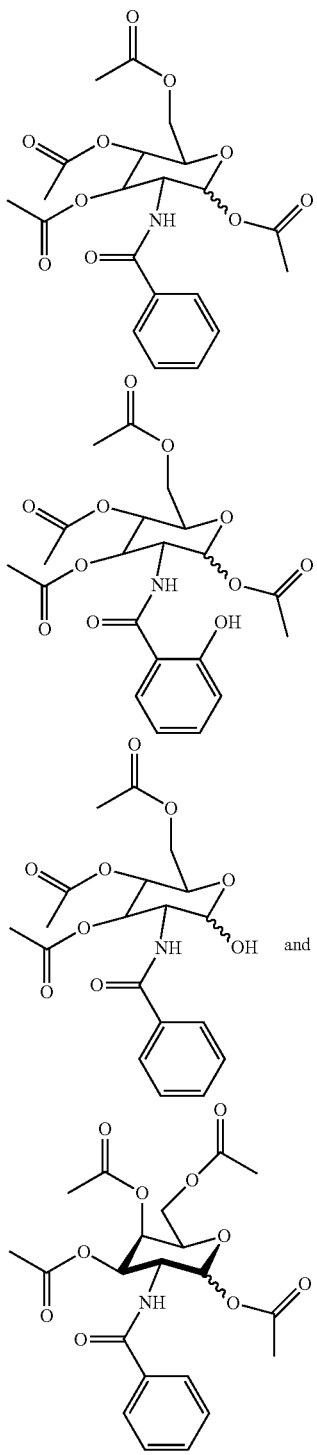

In other aspect, the pharmaceutical composition of the invention may comprise effective amounts of the compound of the invention or a pharmaceutically acceptable salt, solvate or hydrate thereof and pharmaceutically acceptable carrier.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

In another aspect, the compounds of invention or a pharmaceutically acceptable salt thereof may be used in combination with or include one or more other therapeutic agents and may be administered either sequentially or simultaneously by any convenient route in separate or combined pharmaceutical compositions. As used herein, combination of two or more compounds may refer to a composition wherein the individual compounds are physically mixed or wherein the individual compounds are physically separated. A combination use encompasses administering the components separately to produce the desired additive, complementary or synergistic effects. In certain exemplary embodiments, the compound and the agent are physically mixed in the composition. In additional exemplary embodiments, the compound and the agent are physically separated in the composition.

In an exemplary embodiment, an additional bioactive agent may be added to a pharmaceutical composition of the invention. Alternatively, the pharmaceutical composition of the invention may further comprise other drugs for complicated disease treatment with combined use.

In certain exemplary embodiments, the methods may be a combined disease treatments. The disease for the combined treatments may include other types of cancer. Exemplary therapeutic agents or drugs may be, but not limited to, Gefitinib or Erlotonib, for combined treatments of breast cancer, lung cancer and the like.

The pharmaceutical composition of the invention, or the compounds of the invention or a pharmaceutically acceptable salt thereof may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In an exemplary embodiment, the pharmaceutical compositions of the invention may be administered orally, topically, parentally, intravenously or intramuscularly.

In certain embodiments, a compound of the invention is deemed to possess UAP or other inhibitory activity if levels of UAP or other target are observed to be reduced by at least 15% relative to an appropriate control, by at least 20% relative to an appropriate control, by at least 25% relative to an appropriate control, by at least 30% relative to an appropriate control, by at least 35% relative to an appropriate control, by at least 40% relative to an appropriate control, by at least 45% relative to an appropriate control, by at least 50% relative to an appropriate control, by at least 55% relative to an appropriate control, by at least 60% relative to an appropriate control, by at least 65% relative to an appropriate control, by at least 70% relative to an appropriate control, by at least 75% relative to an appropriate control, by at least 80% relative to an appropriate control, by at least 85% relative to an appropriate control, by at least 90% relative to an appropriate control, by at least 95% relative to an appropriate control, by at least 96% relative to an appropriate control, by at least 97% relative to an appropriate control, by at least 98% relative to an appropriate control or by at least 99% relative to an appropriate control. In some embodiments, complete inhibition of glycolysis, UAP and/or other target is required for a compound to be deemed to possess inhibitory activity.

In certain embodiments, a compound of the invention is delivered to a subject (e.g., to a test animal or to a subject or patient) at a dosage of 300 mg/kg/day. In related embodiments, the compounds of the invention can be evaluated over time (duration) and over concentration ranges (potency), with assessment of what constitutes, e.g., an inhibitory activity (e.g., inhibition of UAP), adjusted in accordance with concentrations administered and duration of time following administration. Thus, in certain embodiments, a compound of the invention is deemed to possess inhibitory activity if at least a 20% reduction in glycolysis activity is observed/persists at a duration of time of, e.g., 2 hours, 5 hours, 10 hours, 1 day, 2 days, 3 days, 4 days, 5 days, 6 days, 7 days, 8 days, 9 days, 10 days, two weeks, a month or more after administration of the compound of the invention to a cell or organism. In additional embodiments, a compound and/or pharmaceutical composition of the invention is deemed to be a potent inhibitory agent if UAP inhibitory activity (e.g., in certain embodiments, at least 10%, at least 20%, at least 30%, at least 40%, at least 50%, at least 60%, at least 70%, at least 80%, at least 90%, at least 95%, at least 97%, at least 98%, or at least 99% inhibition of glycolysis and/or UAP) is observed at a formulated concentration of 5 g/kg or less, 1 g/kg or less, 750 mg/kg or less, 500 mg/kg or less, 400 mg/kg or less, 300 mg/kg or less, 200 mg/kg or less, 100 mg/kg or less, 50 mg/kg or less, 25 mg/kg or less, 15 mg/kg or less, 10 mg/kg or less, 5 mg/kg or less, 2 mg/kg or less, 1 mg/kg or less, 750 µg/kg or less, 500 µg/kg or less, 400 µg/kg or less, 300 µg/kg or less, 200 µg/kg or less, 100 µg/kg or less, 50 µg/kg or less, 25 µg/kg or less, 15 µg/kg or less, 10 µg/kg or less, 5 µg/kg or less, 2 µg/kg or less or 1 µg/kg or less when administered to a subject in an effective delivery vehicle. Optional dosage frequencies include once a day, twice a day, once a week, twice a week, three times a week, four times a week, once every two weeks, once or twice monthly, etc.

Methods of the Invention (1) The present invention also provides a method of treating a disease using the compounds disclosed herein. The method comprises administering effective amounts of the pharmaceutical composition comprising the compound of the invention to a subject having a disease, whereby UAP of the hexosamine biosynthetic pathway in glucose metabolism of the subject is inhibited by the compound in the invention.

In one embodiment, the method of treating a disease may comprise administering a therapeutically effective amount of a pharmaceutical composition comprising a compound of Compound I:

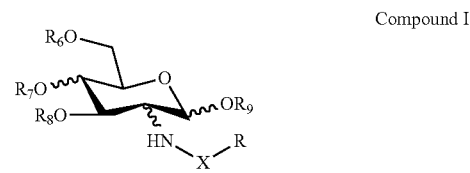

Compound I wherein X is CO, $SO_2$ or $CH_2$;

$R_6$, $R_7$, $R_8$, $R_9$, are each independently H or $CO(CH_2)_n CH_3$;

n is 0-16;

R is selected from the group consisting of

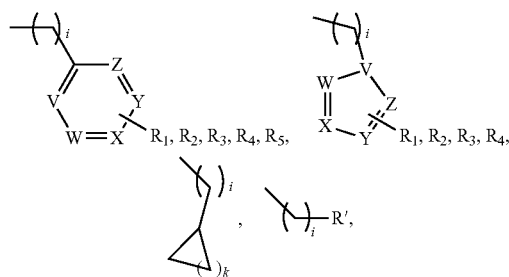

wherein V, W, X, Y, Z are, each independently, C, N, S, or O, $R_1$, $R_2$, $R_3$, $R_4$, $R_5$ are, each independently, absent, —H, —$(CH_2)_m CH_3$ where m=0-6 including branched alkyls, —Br, —Cl, —F, —I, —$NH_2$, —SH, —$NO_2$, —$NHSO_2 R^a$ where $R^a$ is alkyl or branched alkyl, —$SO_2 NHR^b$ where $R^b$ is alkyl or branched alkyl, —OH, —$OR^c$ where $R^c$ is alkyl or branched alkyl or alkyl ester, —$NHR^d$ where $R^d$ is alkyl or branched alkyl or amide, —$OCF_3$, —COOH, or —$COOR^e$ where $R^e$ is alkyl or branched alkyl, R' is substituted or unsubstituted alkyl, which includes heteroatoms NH, O, or S, i is 0 to 16, k is 0 to 10.

In one embodiment, the compound may be selected from the group consisting of:

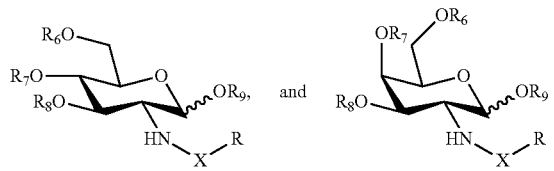 and wherein X is CO or CH$_2$;

R$_6$, R$_7$, R$_8$, R$_9$, are each independently H or CO(CH$_2$)$_n$CH$_3$;

n is 0-16;

R is selected from the group consisting of

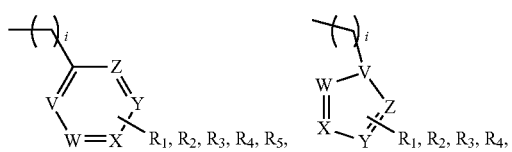

wherein V, W, X, Y, Z are, each independently, C, N, S, or O,

R$_1$, R$_2$, R$_3$, R$_4$, R$_5$ are, each independently, —H, —(CH$_2$)$_m$ CH$_3$ where m=0-6 including branched alkyls, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, R' is substituted or unsubstituted alkyl, which includes heteroatoms NH, O, or S, i is 0 to 16, k is 0 to 10.

In an exemplary embodiment, the compound for methods of treating the disease may be selected from the group consisting of:

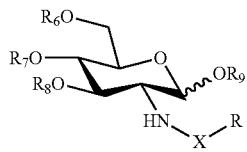

wherein X is CO,

R$_6$, R$_7$, R$_8$, R$_9$, are each independently H or CO(CH$_2$)$_n$CH$_3$, where n is 0-6; and the other groups are described above.

In an exemplary embodiment, the compound for methods of treating the disease may be selected from the group consisting of:

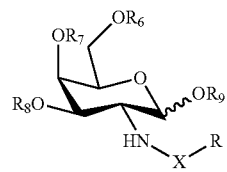

wherein X is CO,

R$_6$, R$_7$, R$_8$, R$_9$, are each independently H or CO(CH$_2$)$_n$CH$_3$, where n is 0-6; and the other groups are described above.

In certain embodiments, X is CO and R is unsubstituted or substituted phenyl group.

In additional embodiments, R$_6$, R$_7$, R$_8$, R$_9$, are each independently H or COCH$_3$.

In an exemplary embodiment, the compound may be selected from the group consisting of:

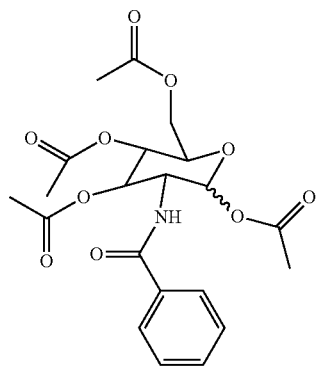

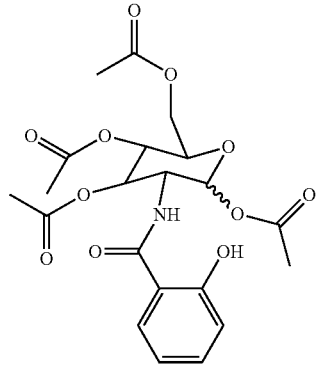

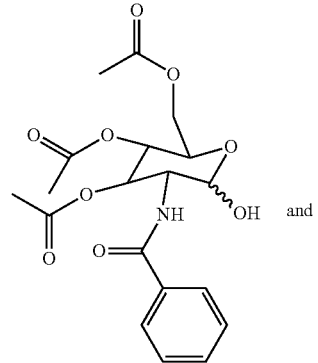 and

-continued

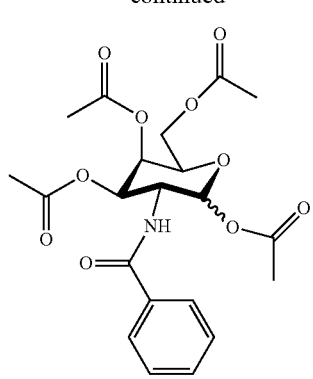

(D)

In one embodiment, the disease may be a cancer. The cancer may be squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas. In certain exemplary embodiments, the cancer which can be effectively treated with the compounds of the invention may be, but not limited to, pancreatic cancer or liver cancer.

In other certain embodiments, the disease may be a metabolic disorder. In certain exemplary embodiments, the disease may be a diabetes or obesity.

In another certain embodiments, the disease may be a neurological disorder. In certain exemplary embodiments, the disease may be Alzheimer's disease.

In certain embodiments, the pharmaceutical composition of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In an exemplary embodiment, the pharmaceutical compositions of the invention may be administered orally, topically, parentally, intravenously or intramuscularly.

(2) The invention also includes a method of controlling glycan production levels within a cell of a subject. The method comprises treating the cell or the subject with a therapeutically effective amount of the pharmaceutical composition comprising the compound of the invention, whereby the glycan produced in the cell of the subject may be controlled. In one embodiment, the compounds of the invention inhibit UAP in HBP, whereby biosynthesis of building units for glycan are blocked or reduced.

In one embodiment, the method of controlling glycan production levels may be directed to a cell in a subject having a disease, such that production of disease-promoting glycans may be effectively suppressed and reduced. The disease may be described above. In certain exemplary embodiments, the methods may be particularly effective to controlling glycan productions in metastatic cancer cells.

(3) The invention further provides a use of the compounds of the invention for screening a test compound, in vitro or in vivo. In particular, the compounds of the invention may be included in a method for screening a selective inhibitor of UAP activity by comparing effects of a test compound from a chemical library with effects of the compounds of the invention, such as $Ac_4Glc2Bz$. The compound of the invention may be a positive control for the screening methods.

In an exemplary embodiment, the method of screening comprises: treating a first group of subject with the compound of the invention; treating a second group of subject with the test compound; and analyzing and determining the level of treatment with the test compound based the level of treatment with the compound of the invention.

In certain embodiments, the method of screening may comprise: treating a first subject group with the compound of the invention; treating a second subject group with the test compound; and determining a level of the treatment of the test compound based on a level of the treatment of the compound of the invention. In certain exemplary embodiments, the level of treatment may be determined by, but not limited to, test results obtained from quantitative cell-free UAP assays, quantitative cell-based UAP assays, quantitative tissue-based UAP assays, cytoxocity assay, cell proliferation assay, qRT-PCR of induced mRNA, knockdown assay, glycosylation profiling, cell adhesion and motility test, drug synergy test or combinations thereof.

Kits

The invention includes a kit comprising an applicator, an instructional material for use thereof, and a compound of the invention. In one embodiment, the instructional material included in the kit comprises instructions for inhibiting UAP in HBP pathway of elevated glucose metabolism. In another embodiment, the instructional material included in the kit comprises instructions for treating a disease or disorder that is associated with an elevated glucose metabolism. Exemplary diseases are described above.

The combinations of the invention may also be presented as a combination kit. When the agents of the combination are administered simultaneously, the combination kit can contain the agents in a single pharmaceutical composition, such as a tablet, or in separate pharmaceutical compositions. When the agents are not administered simultaneously, the combination kit will contain each agent in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

The invention will be further described in the following examples. It should be understood that these examples are for illustrative purposes only and are not to be construed as limiting this invention in any manner.

Examples

Example 1: Cytotoxicity Test

Cells were incubated with a range of concentrations of UAP inhibitors (typically at 0, 10, 25, 50, 100, and 150 µM) for time periods up to 72 hours (depending on the assay) and cytotoxicity was measured using standard assays. For example, esterase-activated fluorescence dyes were used in live/dead assays coupled with quantification by flow cytometry, apoptosis was measured by DNA fragmentation assays, and metabolic activity was measured by the MTT assay.

Example 2: Cell Proliferation Assay

Cells were incubated at a range of concentrations of the UAP inhibitors (typically at 0, 10, 25, 50, 100, and 150 µM) and the number of cells were quantified, typically by automated counting (e.g., with a Coulter Counter Z2 instrument) after 1, 2, 3, or 5 days of exposure.

Example 3: Cell-Free Biochemical Assay

A published method (Chemical Communications, 6976-6978 (2009); Chemistry—A European Journal 16, 13343-13345 (2010)) that measures the biosynthetic conversion of GlcNAc analogs to UDP-GlcNAc by AGX1 and AGX2 (analyzed separately) was followed. Instead of using a single substrate, samples were co-incubated with a standard concentration of GlcNAc-1-P (the natural substrate that was converted to UDP-GlcNAc, which was quantified as the endpoint of the assay) and a 0, 0.25×, 0.5×, 1.0×, 2.5×, and 5.0×-fold excess of Glc2Bz-1-p and/or additional analogs in the present invention.

Gal2Bz (an alternative AGX/UAP inhibitor with potential isoform-specific activity) and Man2Bz (the negative control) were prioritized for testing.

Example 4: Cell Based Assay

Based on previous work of the inventors that discovered that hexosamine analogs were processed by glycosylation pathways at subtoxic levels, cancer cells (e.g., the PANC-1 and SW1990 lines) and healthy cells (e.g., ASCs) were treated with UAP inhibitor analogs over a range of minimally cytotoxic levels (e.g., at 5, 10, 25, and 50 µM, as demonstrated in FIG. 4).

UDP-GlcNAc (and UDP-GalNAc) levels could be measured using standard HPLC assays following published procedures and compared to untreated control cells.

Figure 16B:
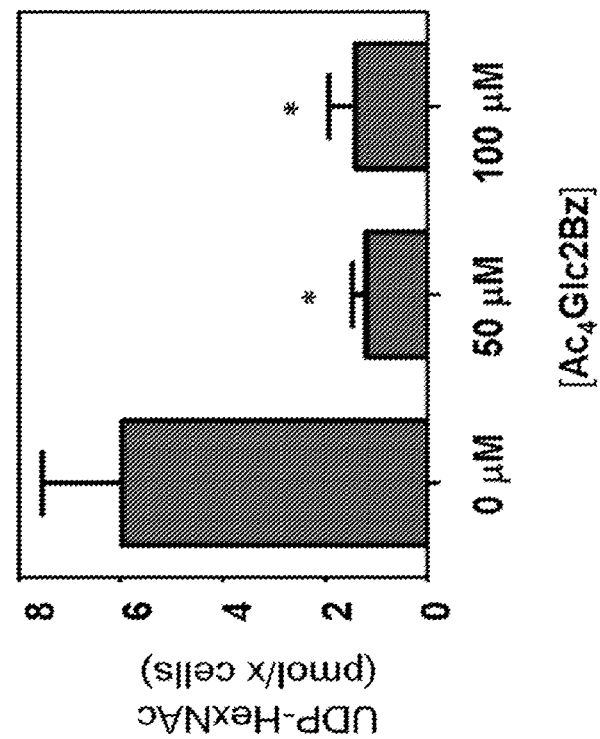
FIGS. 16A-16B show exemplary targeted metabolomics results from primary glioblastoma cells.
Figure 16A:
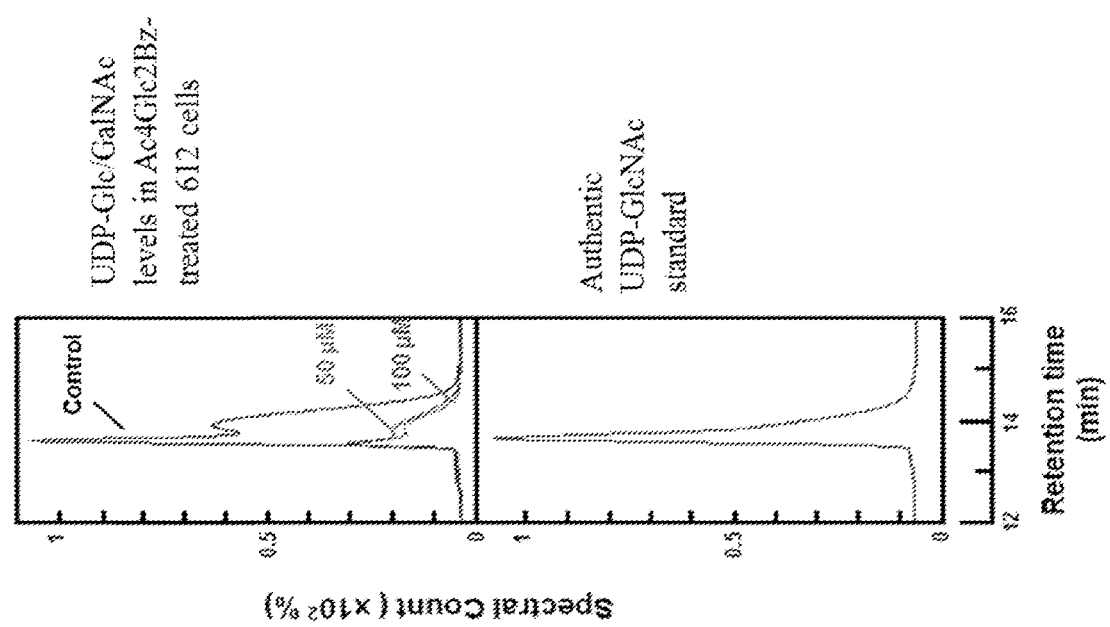

In FIGS. 16A-16B, representative targeted metabolomics results from primary glioblastoma cells were quantitated using LC-MS/MS traces. For example, the 612 cells were treated with 50 µM or 100 µM of Ac$_4$Glc2Bz or non-treated (control). Afterwards, the cell extracts were obtained using Bligh-Dyer extraction and the extracts were analyzed using LC-MS/MS. Twelve 150-mm tissue culture plates were coated with lamin (1 ug/cm$^2$) in PBS for 24 h. 5×10$^6$ 612 cells were seed onto each plate in 20 mL of media for condition tested: DMSO vehicle control (2 plates) (matched to the volume of vehicle used for the 100 µM condition), 50 µM (4 plates), 100 µM (6 plates). Ater 48 h, the plates were cooled for 10 minutes on ice followed by aspiration of the media. The plates were then tilted at 30° for 30 seconds and any remaining media was removed. Plates were washed twice with 10 mL of ice cold PBS (calcium and magnesium ion free). Next, the plates were covered and chilled with dry ice for 10 minutes to completely freeze all of the cells. While freezing the cells, a solution of methanol:H$_2$O (2:0.8) was made and chilled in an isopropyl alcohol-dry ice bath. The plates were transferred to wet ice and 500 µL of the MeOH:H$_2$O solution was added to the plates. Cells were scraped and the were transferred to a 15 mL tube. 500 µL more of the methanol:H$_2$O solution was added again, and any remaining cells were scraped off the plates and were transferred to the 15 mL tubes. Samples, while remaining cold, were sonicated 2-5 times for 1 s and 1 part of chloroform was added to produce a ration of 1:2:0.8 (CHCl$_3$:MeOH:H$_2$O). Samples were briefly vortexed while still cold and 1 part of H$_2$O was added followed by vortexing. 1 more part of chloroform was added and samples were once again vortexed to produce a final ratio of 2:2:1.8 (CHCl$_3$:MeOH:H$_2$O). A white precipitate formed and samples were centrifuged at 5000 rpm for 30 minutes at 4° C. The upper aqeuous phase was obtained and was labeled as 'aqeuous phase 1'. The bottom layer was then obtained by tilting the tube to the side in order to move the interphase disc to the wall of the tube. Half of the organic layer was saved and was labeled as 'organic layer 1' while the other half of the organic layer was dried down and then resuspended in 0.8 parts of 1% formic acid (pH=2) and 2 parts of MeOH. The extraction and isolation of 'aqeuous layer 2' and 'organic layer 2' then proceeded in the same exact manner as above, following with the 3rd extraction utilizing basic conditions (2% ammonium hydroxide pH=9). Finally, all three aqeuous layers that were obtained were lyophilized and all the organic layers were evaporated. DNA quantity from the interphase disc was determined using a fluorescent assay (SIGMA). It is noted that DNA is expected in the interphase disc, and reference is made to Sapcariu et al. *Methods X* 1: 74-80. The aqeuous layers were combined after normazling reconstitutions to the quantities of DNA obtained for each condition tested. UDP-HexNAc analysis was performed using an Agilent 6490 Triple Quadrupole (QQQ) mass spectrometer with Agilent 1290 HPLC. HPLC conditions: Zorbax SB-C18, RRHD 1.8 µm, 2.1×150 mm (Agilent 859700-902), A: 5% MeOH+15 mM Acetic Acid, B: Isopropanol, 0→50% B in 14 minutes. MS detection utilized ESI in negative mode and tandem mass spec with CID. Experiments and UDP-HexNAc quantization were repeated three times.

As shown in FIG. 16A, traces for UDP-GlcNAc and UDP-GalNAc (i.e. UDP-HexNAc) were obtained from LC-MS/MS separation, and peaks for UDP-HexNAc were substantially lower in Ac$_4$Glc2Bz treated cell extracts. In FIG. 16B, peaks were quantitized and normalized based on the amount of UDP-HexNAc from the non-treated cell extract, and the results are presented in a graph. In particular, the quantitized amount of HexNAc, particularly the amount of UDP-GlcNAc, was reduced nearly 4-fold compared to that from the non-treated cell, when 50 µM Ac$_4$Glc2Bz was administered. As such, the product of UAP1/2 (i.e., UDP-Glc/GalNAc) could be reduced by UAP inhibitor analogs of the invention during late stage inhibition of the HBP pathway.

The expression of each UAP isoform also could be measured by qRT-PCR (J Biol Chem., 281, 27016-27028 (2006)) and was correlated with cytotoxicity and the ability of different analogs (e.g., Ac$_4$Glc2Bz or Ac$_4$Gal2Bz) to alter UDP-Glc/GalNAc levels in the respective cell types.

Figure 20A:
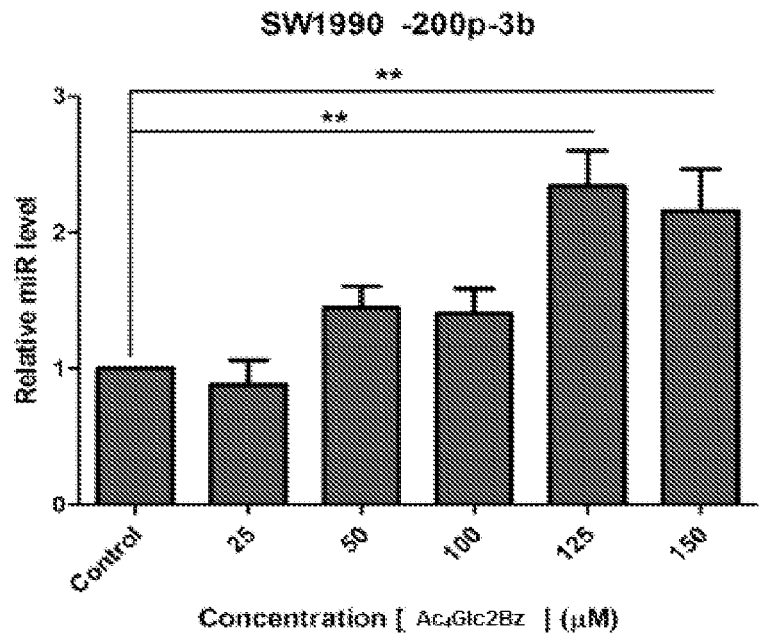
FIGS. 20A-20C show qRT-PCR analysis of microRNA expression following treatment with different concentrations of Ac$_4$Glc2Bz, for SW1990 cells of 200p-3b (FIG. 20A); for 612 cells of 191b-5p (FIG. 20B); and for SW1990 cells of 181p-5p (FIG. 20C).
Figure 20B:
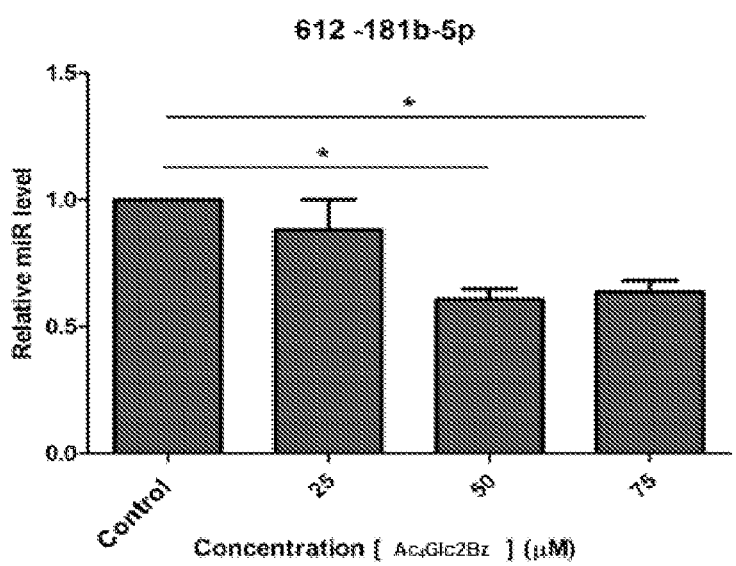
Figure 20C:
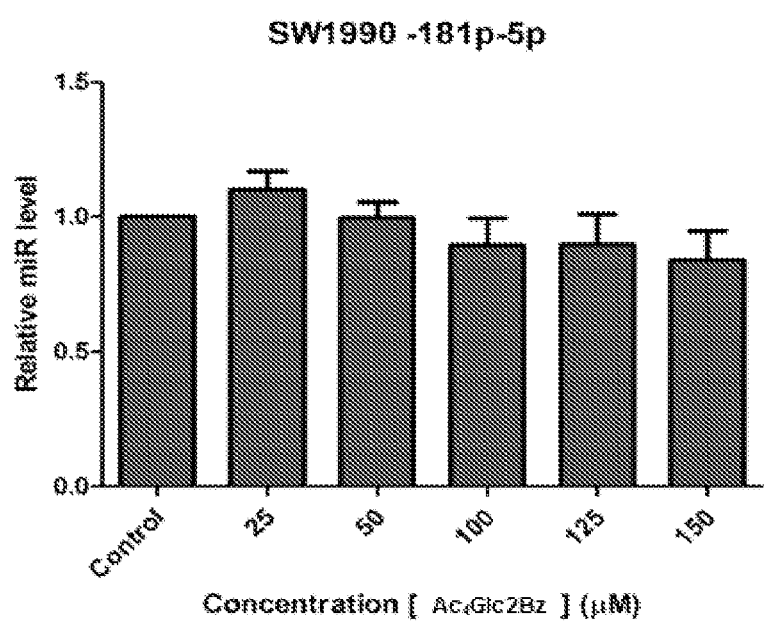

For example, qRT-PCR analysis revealed trends in microRNA expression upon treatment with Ac$_4$Glc2Bz (FIGS. 20A-20C). The microRNAs analyzed were chosen because they regulated different aspects of cancer cell glycosylation. 3×10⁵ cells per well in a 6-well plate were seeded along with the concentrations of Ac$_4$Glc2Bz indicated. Glioblastoma cells were placed on 6-well plates precoated with laminin (1 ug/cm²). After 48 h, miRNA was extracted using a miRNeasy kit (Qiagen), followed by cDNA synthesis and qrt-PCR using miRCURY LNA™ Universal RT microRNA PCR Starter Kit (Exiqon). As shown in FIG. 20A-20C, from Ac$_4$Glc2Bz treated cells (e.g. SW1990 and 612 cell), microRNA could be modulated by UAP inhibitor analogs (e.g. Ac$_4$Glc2Bz). These results also implicated involvement of microRNAs in further diseases and disorders related to HBP pathways.

Example 5: AGX/UAP Knockdown

AGX inhibitors have previously been observed to impede flux through the HBP by reducing AGX1 and AGX2 levels, and such inhibition can be observed by using shRNA methods that follow standard knockdown procedures as previously described (*J Biol Chem* 281, 27016-27028 (2006)).

Figure 22A:
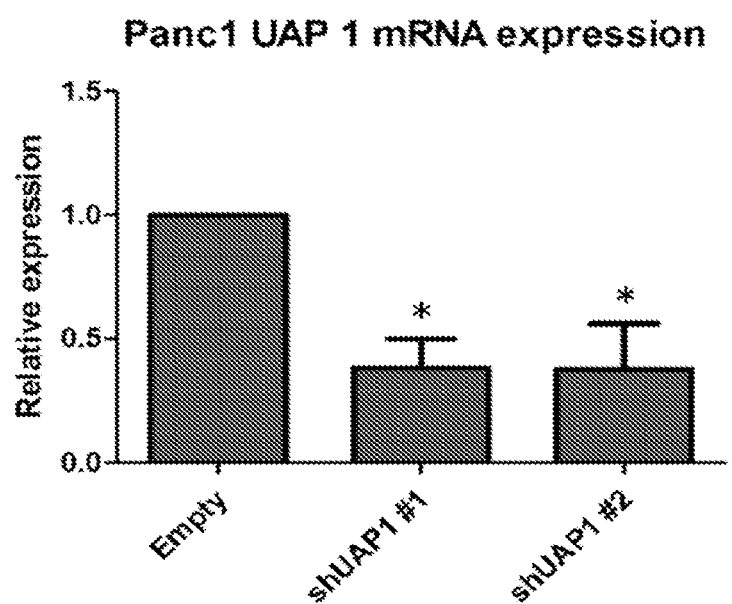
FIG. 22A-22B shows UAP1 mRNA expression results following shRNA knockdown of UAP1 via lentiviral methods, in PANC-1 cells treated with Ac$_4$Glc2Bz (n=3)

In FIG. 22A, results of relative expression levels of UAP 1mRNA expression are shown where shRNA knockdown of UAP1 was performed using lentiviral methods in PANC-1 cells (n=3). 1×10⁵ PANC-1 cells were seeded into a 6 well plate and were allowed to adhere for 24 h. Lentiviral shRNA knockdown of UAP1 was achieved by using TRC1 constructs (TRCN0000072368 and TRCN0000072370) and TRC2 constructs (TRCN0000333729, TRCN0000344945, TRCN0000333815). Lentiviral particles contain empty vector backbones were used as controls. Transduced cells were then selected for 1 week using puromycin (0.35 μg/mL), followed by isolation of mRNA using a RNeasy Mini Kit (Qiagen), cDNA synthesis using High-Capacity cDNA Reverse Transcription Kit (Life Technologies), and qrt-PCR analysis of UAP1 expression using PrimePCR™ SYBR® Green Assay: UAP1 Human primer (10025636 BioRad) and SYBR® Green PCR Master Mix (Life Technologies) and GAPDH as a control (provided by the Jennifer H. Elisseeff lab).

Figure 22B:
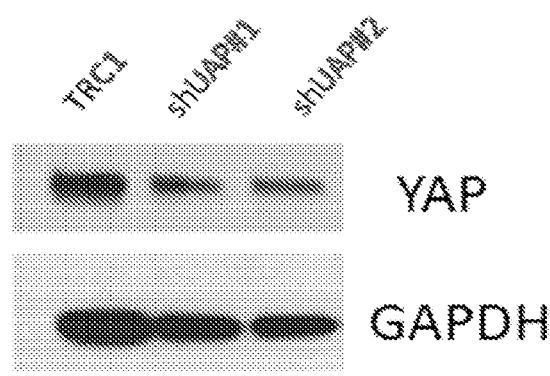

In addition, in FIG. 22B, YAP western blot results from Ac$_4$Glc2Bz cells were obtained where shRNA knockdown of UAP1 was performed using lentiviral methods in PANC-1 cells (n=3). Similar to above, UAP1 in PANC-1 cells was knocked down using lentiviral vectors followed by 1 week selection using puromycin. Proteins were obtained by lyzing cells in RIPA buffer (SIGMA) supplemented with Protease Inhibitor Cocktail (1:100), Phosphatase Inhibitor Cocktail 2 (SIGMA) (1:100), and Phosphatase Inhibitor Cocktail 3 (SIGMA)(1:100). SDS-PAGE was performed followed by western blotting for YAP (Cell Signaling) and GAPDH (Cell Signaling).

Example 6: Characterization of Cell Surface Glycan after Treatment

The SW1990 line was prioritized for testing because (i) pancreatic cancer remains largely untreatable and any insights in the role of glycosylation would be valuable. Prioritized samples included untreated cells, cells treated with two levels of 2 or 3 inhibitors (e.g., 10 and 50 μM of Ac$_4$Glc2Bz, Ac$_4$Glc2Bz(2-OH), and/or Ac$_4$Gal2Bz) or with siRNA against UAP1 and UAP2.

(a) Cell surface N-Glycans. After two days of incubation with analog (a length of time sufficient to observe maximal "metabolic glycoengineering" effects (Biotechnol Bioeng 85, 394-405 (2004); Biotechnol Bioeng 109, 992-1006 (2012); Mol Cell Proteomics, 10.1074/mcp.M1112.017558 (2012); Glycobiology 19, 1382-1401 (2009); Nature Protocols 2, 1585-1602 (2007)), cells treated with PNGaseF, N-glycans were collected, and analyzed by following a recently developed protocol that optimizes sialic acid detection and quantification (*Anal Chem* 85, 3606-3613 (2013)). As previously developed, automated methods were used to analyze mass spectroscopy data to detect phenyl-modified sugars in glycan structures. This analysis was valuable to monitor whether any phenyl-modified analog was biosynthetically processed (instead or in addition to inhibiting UAP) and incorporated into cellular glycans.

Figure 18A:
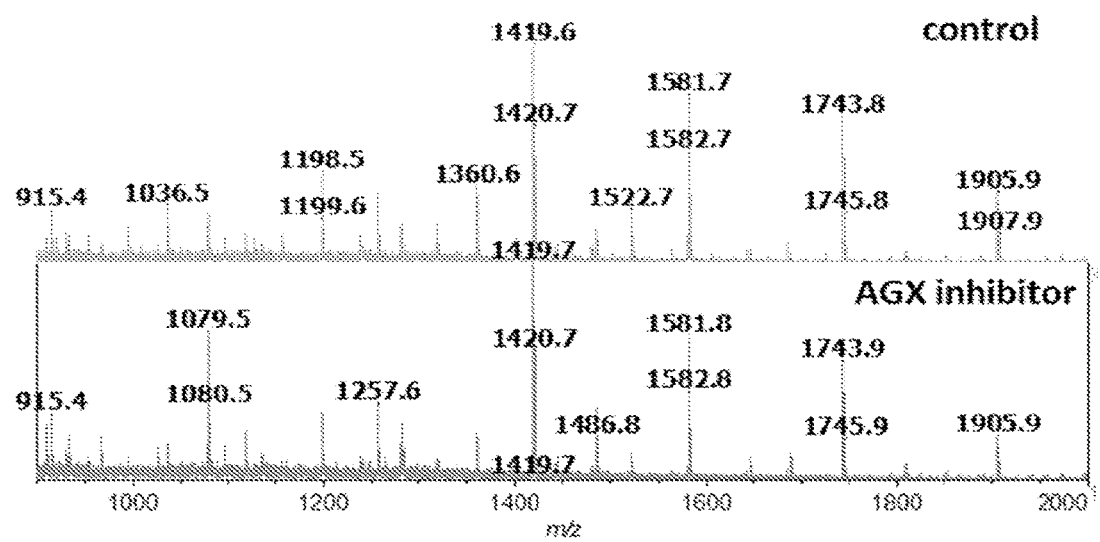
FIGS. 18A-18B present mass spectrometry results showing levels of N-glycans (lower molecular weight glycans) and high molecular weight glycans following treatments with Ac$_4$Glc2Bz (100 µM) in SW1990 cells.
Figure 18B:
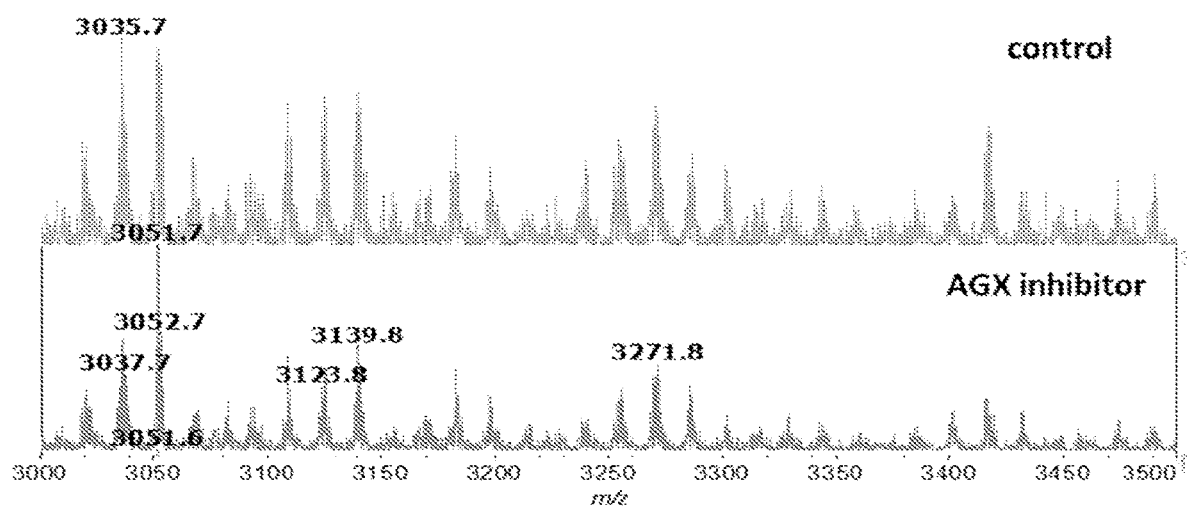

For example, as shown in FIGS. 18A-18B, SW1990 cells were treated with Ac$_4$Glc2Bz (100 μM), and the cell extracts were analyzed by mass spectrometry.

In the regions of peaks for N-glycans (lower molecular weight glycans), amplitude of each peak was not significantly reduced (FIG. 18A), whereas in the regions of peaks for high molecular weight glycans, which might include highly branched structures associated with cancer, quantitative changes were identified. Those results likely meant that high levels of UDP-GlcNAc were required only for the production of highly-branched disease-associated N-glycans; about 25% residual level of UDP-GlcNAc (shown in FIGS. 18A-18B) was sufficient for maintenance of "healthy" N-glycans. In addition, all these results indicated the availability of a safety level or dose for the UAP inhibitor drug candidates that would only impact disease-associated types of glycosylation.

(b) Cell surface O-Glycans. Chemical cleavage such as reductive alkaline β-elimination was used to remove cell surface O-glycans (Nature Protocols 2, 1585-1602 (2007)), which were analyzed by mass spectrometry as described for the N-glycans (Anal Chem 85, 3606-3613 (2013)).

(c) Intracellular O-GlcNAcylation. O-GlcNAc changes are dynamic and occur more quickly than surface changes (Essentials of Glycobiology, Cold Spring Harbor Laboratory Chapter 18, http://www.ncbi.nlm.nih.gov/books/NBK1954/ (2009)), therefore analyses were performed in time course at 0.5, 1.0, 4.0 12, 24, and 48 h after treating cells with the maximal non-toxic level of analog (e.g., 25 or 50 μM). Global changes were monitored by Western blots; the goal was to verify that such changes occurred, not to thoroughly characterize each change at a biochemical level. Two specific endpoints, however, were monitored because they offered an explanation for the cytotoxicity observed in FIGS. 3 and 4: (i) heat shock proteins whose O-GlcNAc status could affect cellular responses to stress (J Biol Chem 279, 30133-30142 (2004); J Biol Chem 285, 39096-39107 (2010)) and (ii)O-GlcNAc modification of serine 529 of phosphofructokinase 1 (PFK1), which were analyzed using a published procedure (Science 337, 975-980 (2012)).

Figure 17A:
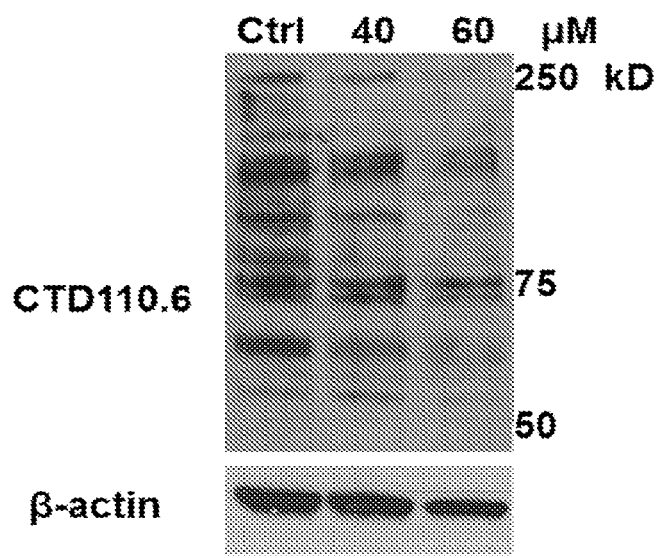
FIGS. 17A-17D show that O-GlcNAcylation changed upon administration of Ac$_4$Glc2Bz, in a dose-dependent manner. Exemplary CTD110.6 protein expression results were obtained for 612 cells (FIG. 17A); GS1049 cells (FIG. 17B); SE1990 cells (FIG. 17C); and PANC-1 cells (FIG. 17D) with either 40 µM or 60 µM Ac$_4$Glc2Bz.
Figure 17B:
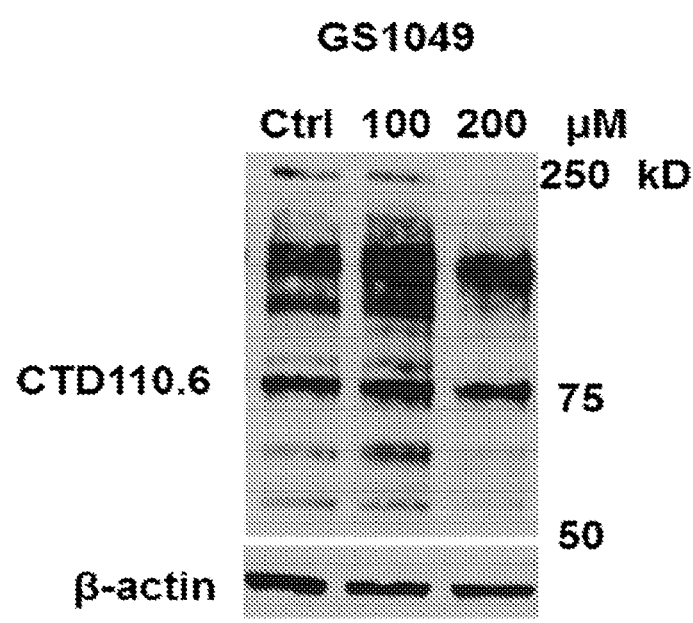
Figure 17C:
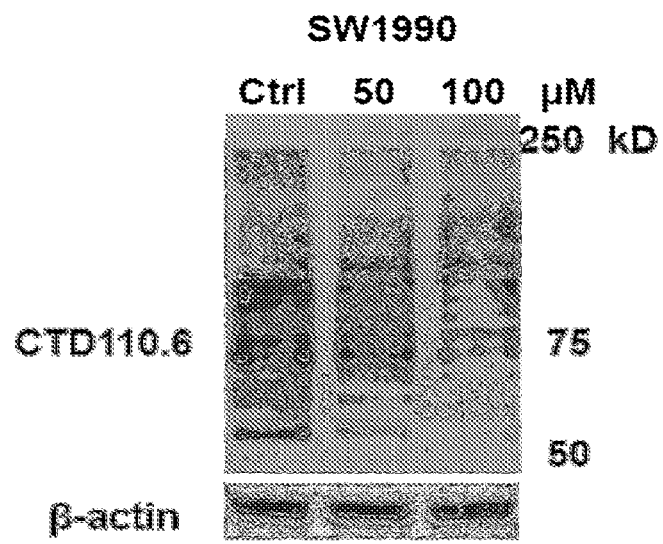
Figure 17D:
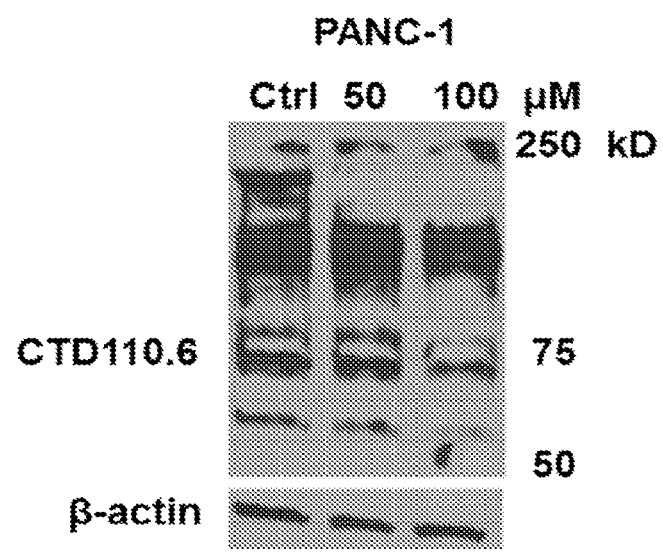

For example, as shown in FIG. 17A-17D, Ac$_4$Glc2Bz could change O-GlcNAcylation in a dose-dependent manner in each cell of 612 cells (FIG. 17A); GS1049 (FIG. 17B); SW1990 (FIG. 17C) and PANC-1 (FIG. 17D). In particular, the band intensities of CTD110.6 (anti-O-GlcNAc antibody) from each treated cell decreased as the concentrations of Ac$_4$Glc2Bz treatment were increased. 3×10⁵ cells were plated in 6-well plates, with 2 wells per condition tested as indicated in FIG. 17A-D. After 48 h, proteins were collected after freezing for 15 minutes at −80° C. using extraction buffer consisting of 20 mM TrisHCl, pH 7.5, 1% v/v NP-40, 2 mM EDTA, 0.1 mM phenylmethylsulfonyl fluoride, phosphatase inhibitor cocktails 2 and 3 (1×) (SIGMA), ThiametG (10 nM) (Cayman Chemical), β-hexosaminidase inhibitor (5 μM) (Millipore), sodium fluoride (1 mM), and β-glycerophosphate (1 mM). The lysed cells were scraped, collected, and incubated on ice for 20 minutes while vortexing for 5-10 s ever 5 minutes. Samples were sonicated for 5 seconds and then centrifuged at 14,000 RPM for 20 minutes at 4° C. The supernatant was removed, normalized to 1 mg/mL, and 20 µg was loaded onto a 7.5% SDS-PAGE gel. The proteins were transferred to a nitrocellulose membrane which was then blocked with a solution of 3% milk in TBST for 1 hour. The membrane was washed with TBST (3×10 minutes) and then probed with CTD110.6 (provided by the Johns Hopkins Cardio PEG core) (1:2000) in 3% BSA in TBST overnight. The membrane was washed with TBST (3×10 min.) and probed with the secondary antibody (provided by the John Hopkins Cardio PEG core) (1:5000), in 3% BSA in TBST for 1 hours. The membrane was washed with TBST (3×10 min.) and then with TBS (10 min.). The membranes were then exposed after adding SuperSignal™ West Pico Chemiluminescent Substrate.

As such, UAP inhibitor analogs or compounds of the present invention were identified to provide the intended effect of inhibiting UAP1/2 activity and subsequently reducing UDP-GlcNAc levels during O-GlcNAc protein modification, as indicated as "Late Stage Inhibition" in FIG. 2.

Example 7. Cell Adhesion and Motility Test

Standard cell adhesion and wound healing assays were performed upon SW1990 and PANC1 cell lines pretreated for two days with $Ac_4Glc2Bz$ and 2 to 4 other analogs (such as $Ac_4Gal2Bz$ or $Ac_4Glc2Bz(2-OH)$). In these adhesion assays, cells were added to tissue culture plastic that was uncoated or coated with BSA (to block adhesion) or pro-adhesive ECM components including fibronectin, collagen, and Matrigel. The number of cells attached to each plate was quantified in a time course after 15, 30, or 60 minutes.

Similarly, coated surfaces were used for a wound healing assay that adhered to a standard protocol (Cell Migration Methods in Molecular Biology 294, 23-29 (2005)) with the experiment designed to identify full closure of the "wound" after about 12 h. Finally, if an effect was observed in these experiments, that were conducted on flat surfaces, a modified Boyden chamber experiment was conducted to test the ability of cells to migrate through 3-dimensional matrigel, using published protocols (*J Med Chem* 51, 8135-8147 (2008)).

Example 8. Drug Synergy Test

Gefitinib (IEE Proceedings-Systems Biology 153, 457-466 (2006)) and Erlotonib (J Surg Res 135, 195-201 (2006)) were tested at concentrations ranging from 0.01 to 10 µM in PANC1 and SW1990 cells that had been pre-treated for 0, 1, or 2 days with $Ac_4Glc2Bz$ (or other analog); in control experiments, the sugar analog was maintained or removed from the cells during Gefitinib/Erlotonib treatment. At endpoints of the experiments, growth inhibition was measured by using cell counts; EGFR and STAT3 phosphorylation were detected by western blots; and BCL3, MMP2, and MMP7 mRNA levels were measured by qRT-PCR (*J Biol Chem* 281, 27016-27028 (2006)). Accordingly, synergy between the UAP/AGX inhibitor and established drugs was quantified using the Combination Index (*Cancer Res* 70, 440-446 (2010)). In cases where reduced MMP2 and MMP7 expression was observed, activities were tested by zymography and transmigration in the Boyden chamber assay (*J Med Chem* 51, 8135-8147 (2008)).

Example 9. Lectin Binding Assay

Lectin binding could provide additional insight into glycosylation patterns that might be altered following treatment with $Ac_4Glc2Bz$ (FIGS. 19A-19D). Such experiments tested patterns of glycosylation regulated by miRNAs, as well as those in cancer.

In each case of SW1990, PANC-1, 612 and GS1049 cells (respectively shown in FIGS. 19A-19D), PSA could indicate high mannose levels caused by impaired MANIA expression, which is regulated by miR-181. When PSA staining was observed as a result of increased PSA binding, that implied increased MANIA expression and decreased miR-181 expression. In addition, loss of UEA binding was a strong marker for the EMT. Because the miR-200 target, FUCA2, decreased UEA binding, FUCA2 upregulation likely indicated decreased miR-200 family expression; meanwhile, increased UEA binding indicated less EMT/ aggressiveness and implied decreased FUCA2 expression and increased miR-200 expression and/or activity. Because the miR-200 family also targets important proteins central to the EMT cascade, an increase in UEA strongly indicated reduced metastatic ability (e.g. miR-200f up-regulation meant decreased ZEB1 expression, since ZEB1 is a target for the miR-200 family). SNA or SAN binding was correlated with increased alpha 2,6 sialylation, which could inhibit pancreatic cancer and glioma growth (*PLoS One.* 2014; 9(5): e98595; *Pancreas.* 2014 January; 43(1):109-17; *Cancer Res.* 2001 Sep. 15; 61(18):6822-9).

As shown in FIGS. 19A-19D, UAP inhibitors of the present invention were observed to have an effect on cancer-related cell surface glycans in many ways, and these experiments importantly provided a window into the current physiological state of a cell at any moment in time, since miRs that regulate glycosylation overlap with many targets of the proteome that are important in cancer. Those trends indicated by the changes in glycosylation, which reflected possible changes in miRNA profiles, suggested that Ac4Glc2Bz exerted a profound impact on cancer cell aggressiveness.

Example 10. YAP and c-MYC Expression

As described above in Example 5, $Ac_4Glc2Bz$ was observed to reduce protein expression of YAP/GAPDH in a dose-dependent manner. $Ac_4Glc2Bz$ could further reduce c-MYC expression in a dose-dependent manner across cells lines such as SW1990, PANC-1, 612 and GS cells (FIGS. 21A-21D). Proteins from treated cells were obtained by lysing cells in RIPA buffer (SIGMA) supplemented with Protease Inhibitor Cocktail (1:100), Phosphatase Inhibitor Cocktail 2 (SIGMA) (1:100), and Phosphatase Inhibitor Cocktail 3 (SIGMA)(1:100). SDS-PAGE was performed followed by western blotting for c-MYC (Cell Signaling) and β-actin (SIGMA).

Figure 10A:
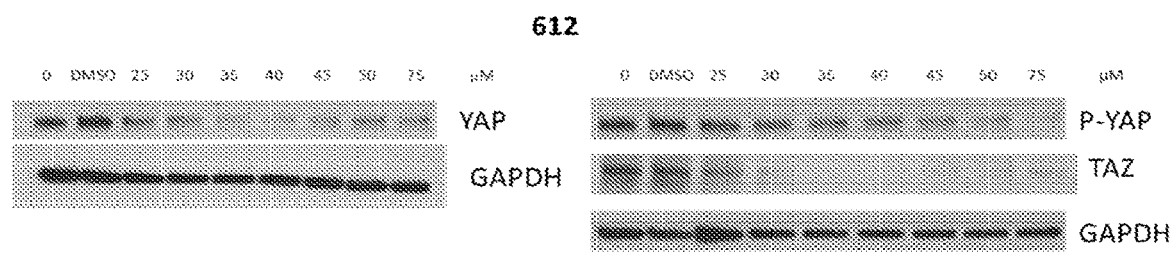
FIGS. 10A and 10B show the western blot results from primary glioblastoma cell lines 612 (FIG. 10A) (these cells were a kind gift of Dr. Quinones-Hinojosa (School of Medicine, Johns Hopkins University), who obtained the cells from cancer patients) and GS1049 (FIG. 10B) that were incubated for 48 h with Ac$_4$Glc2Bz at the indicated concentrations. Each cell line was probed for the proteins Yes Associated Protein (YAP), transcriptional coactivator with PDZ-binding motif (TAZ), phosphorylated Yes Associated Protein (p-YAP), and Glyceraldehyde 3-phosphate dehydrogenase (GAPDH control). Ac$_4$Glc2Bz virtually abolished protein expression of YAP/TAZ in a dose dependent manner. YAP/TAZ are two key mediators that act to suppress the Hippo pathway, which helps to promote oncogenesis, metastasis, and cancer cell survival in circulation. Until now, there were no known small molecule pharmacological agents capable of decreasing YAP/TAZ expression. These studies helped illustrate the extraordinarily powerful potential of UAP1/2 inhibitors as truly disease modifying candidates, especially in cancer.
Figure 10B:
Figure 11:
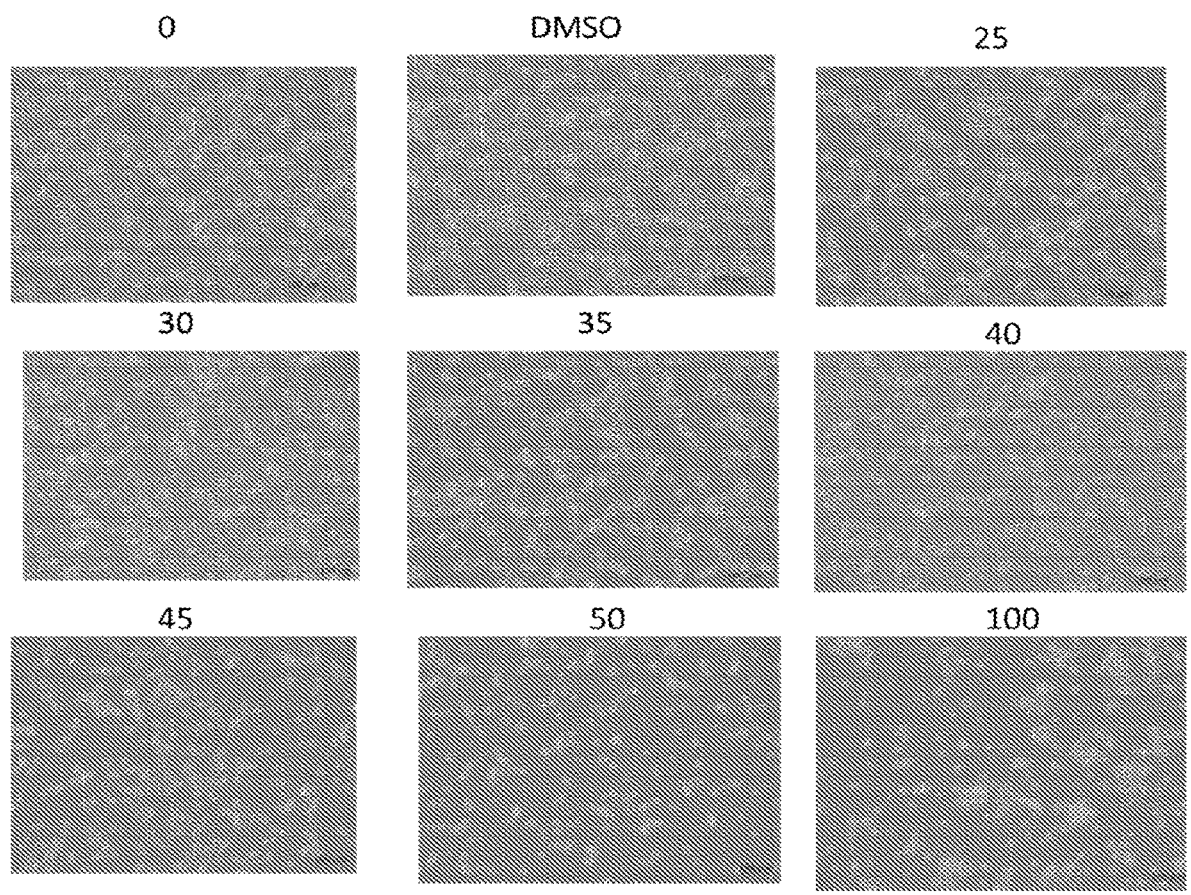
FIG. 11 shows typical phenotypic results that were observed under a microscope after primary glioblastoma cell line 612 had been treated for 48 hours with Ac$_4$Glc2Bz. The images reveal a striking reduction in cell densities in a dose dependent manner. Furthermore, cell morphologies were grossly altered as concentrations of Ac$_4$Glc2Bz were increased, which likely indicated severe metabolic stress, induction of apoptosis, and possibly altered adhesion.
Figure 12:
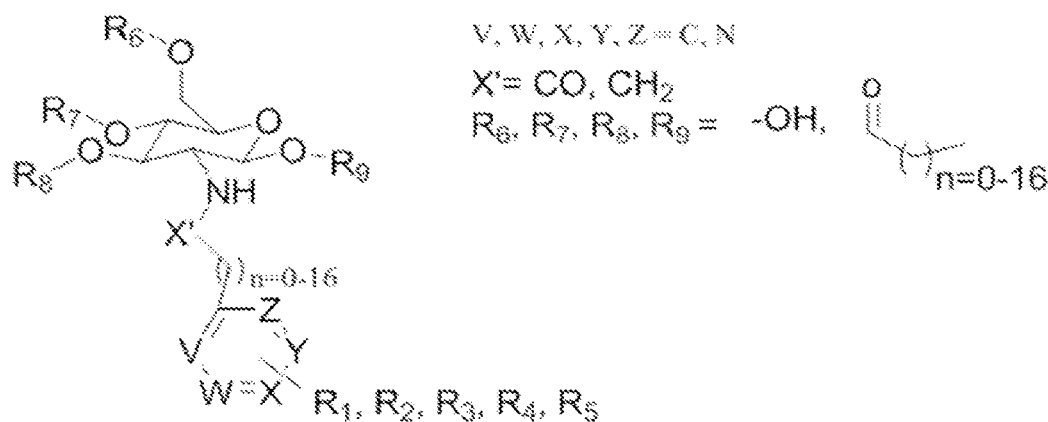
FIG. 12 shows an exemplary six-member aromatic hexosamine compound of the invention as UAP inhibitor.
Figure 13:
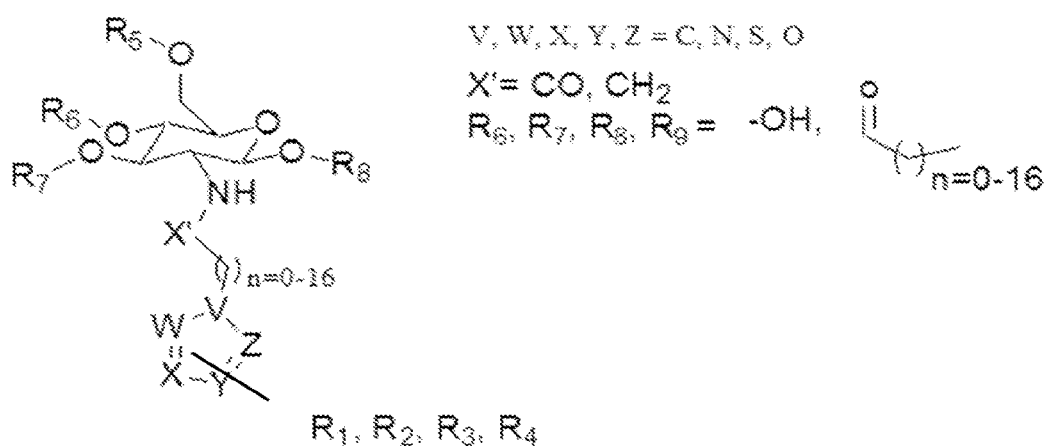
FIG. 13 shows an exemplary five-member aromatic hexosamine compound of the invention as UAP inhibitor.
Figure 14:
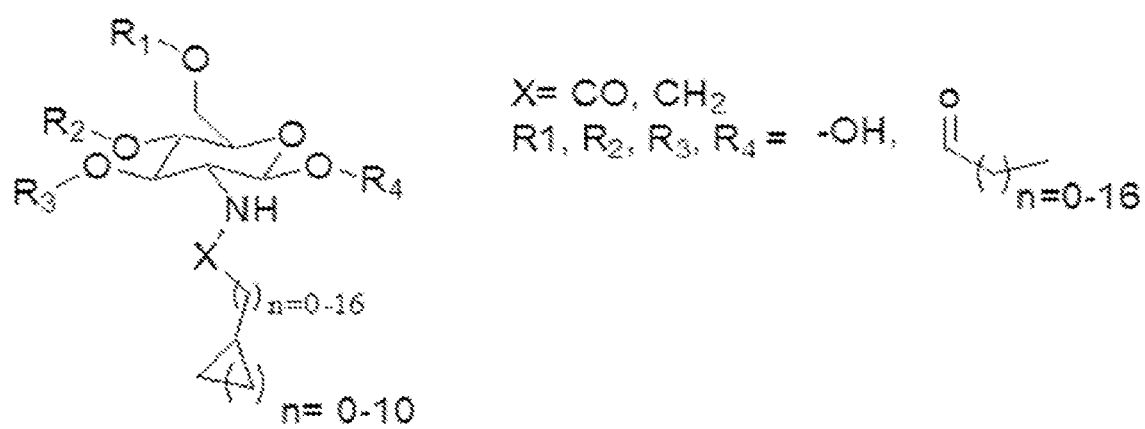
FIG. 14 shows an exemplary non-aromatic ring hexosamine compound of the invention as UAP inhibitor.
Figure 15:
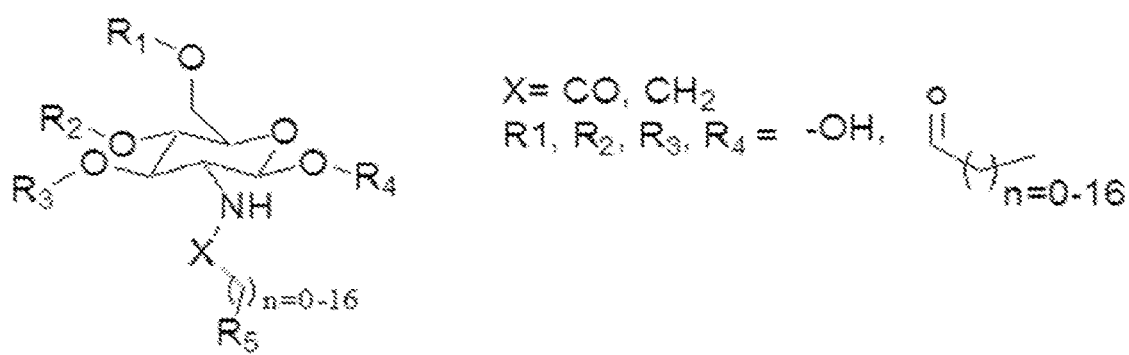
FIG. 15 shows an exemplary alkyl amine or non-amide hexosamine compound of the invention as UAP inhibitor.

Those results suggested a connection between surface glycosylation, particularly O-GlcNAcylation of c-MYC, miRNAs, and signaling molecules that regulated cancer, in particular through the Hippo pathway that YAP/TAZ regulate. Indeed, YAP/TAZ was shown to be down-regulated in a dose-dependent manner using the UAP inhibitor of the invention (FIGS. 10A and 10B) and further regulated expression of c-MYC through miRNAs.

Example 11. DNA Methylation Assay

Figure 23:
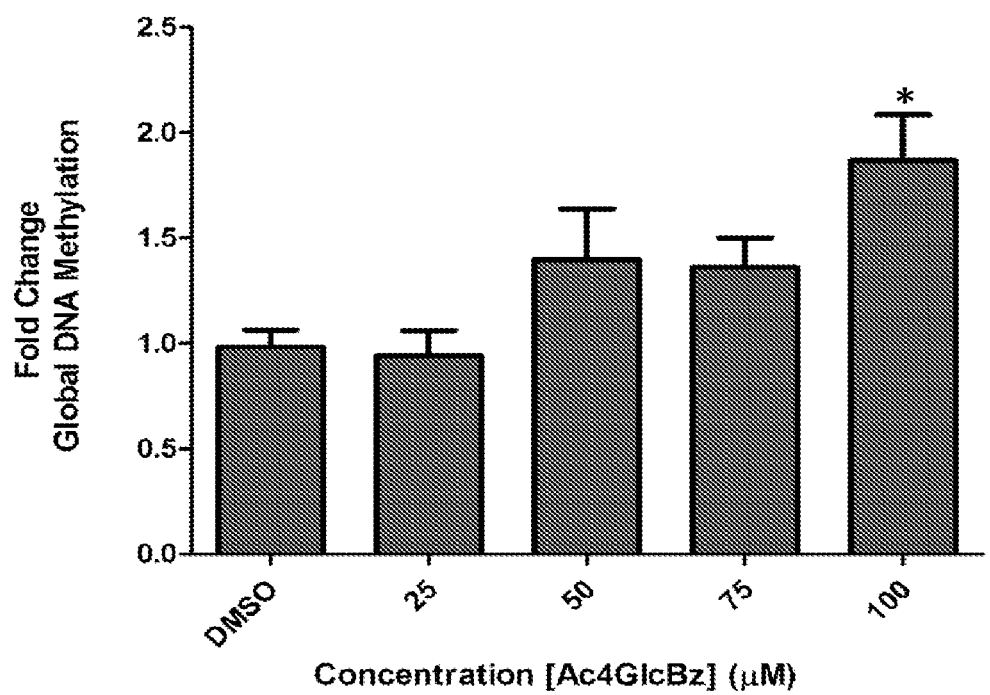
FIG. 23 shows global DNA methylation alterations observed following treatment Ac$_4$Glc2Bz at difference concentrations.

As shown in FIG. 23, $Ac_4Glc2Bz$ was observed to promote global DNA methylation at higher doses. In 6-well plates, SW1990 cells were seeded ($3 \times 10^5$) and were treated with $Ac_4Glc2Bz$ at the indicated concentrations. DNA from treated cells was isolated using a FitAmp Blood and Cultured Cell DNA Extraction Kit (Epigentek) followed by colormetric determination of global methylation using a MethylFlash™ Methylated DNA Quantification Kit (Epigentek). These results suggested that sugar metabolism was likely linked to epigenetic modifications. For instance, by reducing flux through the HBP, UAP inhibitors could exert epigenetic effects, as global DNA methylation was increased as shown in FIG. 23. Although hypermethylation of promoter sites of tumor suppressors might be common in cancer at a global scale, cancer cells are almost always characterized by hypomethylation, which the current UAP inhibitors appeared to be reversing (*Epigenomics*. 2009 December; 1(2): 239-259; *Oncogene*. 12 Aug. 2002, Volume 21, Number 35, Pages 5400-5413).

Example 12. Synthesis

Reagents

Unless otherwise stated, all reagents and starting materials were purchased from Sigma Aldrich.

MeOH: methanol $CH_3ONa$: Sodium methoxide (25% wt solution)

EtOAc: ethyl acetate IPA: isopropyl alcohol

TEA: triethylamine DMAP: 4-dimethylamino pyridine

THF: tetrahydrofuran

TBTU: O-(Benzotriazol-1-yl)-N,N,N',N'-tetramethyluronium tetrafluoroborate

Hexosamine hydrochlorides and 1,3,4,6-tetra-O-acetyl-α-D-glucosamine HCl were purchased from Carbosynth 1) Synthesis of Benzyl-Derivatized Hexosamine Analogs

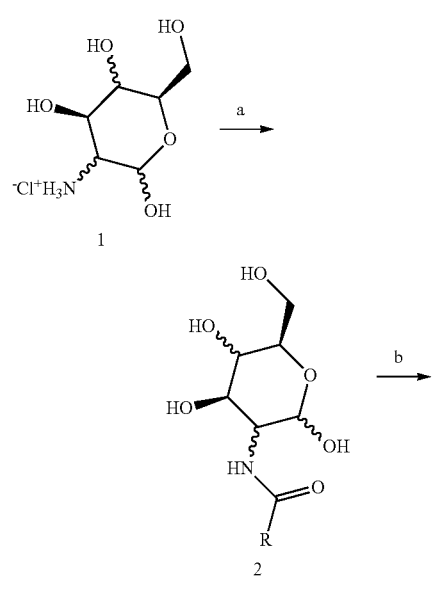

1

2

2a: Glc, R = Ph
2b: Gal, R = Ph
2c: Man, R = Ph
2d: Glc, AD$_3$

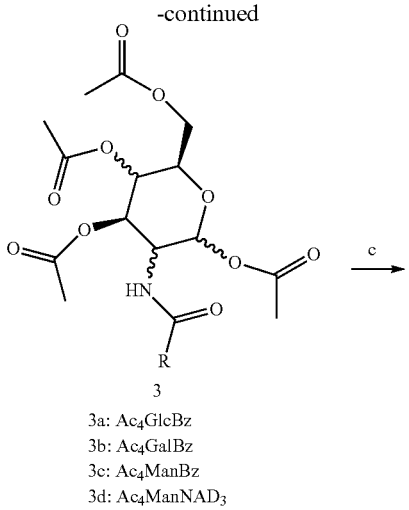

3

3a: Ac$_4$GlcBz
3b: Ac$_4$GalBz
3c: Ac$_4$ManBz
3d: Ac$_4$ManNAD$_3$

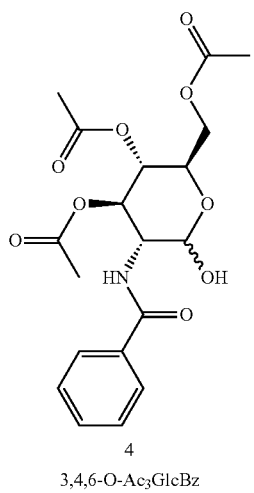 [SMILES: CC(=O)OC[C@H]1OC(O)[C@H](NC(=O)c2ccccc2)[C@@H](OC(C)=O)[C@@H]1OC(C)=O]

4

3,4,6-O-Ac$_3$GlcBz

General Scheme for Synthesis of Analogs via Anhydrides (2a-d): Hydrochloride salt of each hexosamine (1 eq.) was chosen and stirred in anhydrous MeOH for a concentration of 100 mg/mL under an inert atmosphere of argon. $CH_3ONa$ (25 wt. %) was added (1.1 eq), and the solution was stirred for 10 minutes. Benzoic anhydride (2a-2c) (1.4 eq) or acetic anhydride-d6 were added and the reaction was stirred overnight at room temperature. The reactions were then filtered over a pad of celite, washed with MeOH, and concentrated by rotavap. The isolated products were characterized by TLC using EtOAc:IPA:H$_2$O (9:3:1). Some of 2a was set aside and also was characterized; 2b-d were directly used for the next step without characterization. 2a was purified on a silica gel column w/ 0.1TEA using EtOAc:IPA:H$_2$O (9:3:1). A white solid was obtained. The solid material was stirred for 1 hour in EtOAc (200 mL), filtered, and washed with EtOAc. The solid material was then triturated in pure hexanes at 35° C. for 2 hours. The white solid material was filtered, washed with hexanes, dried overnight, and characterized by $^1$H NMR and $^{13}$C NMR.

General Scheme for Analog Esterification with Acetates (3a-3d): 2a-2d were stirred in pyridine (40 mg/mL concentration) along with a catalytic amount of DMAP. The solution was cooled in an ice bath for 15 minutes. Acetic anhydride (8 eq.) was added and the reaction was stirred overnight at room temperature. The pyridine was evaporated off and the residue was dissolved in EtOAc. The collected organics were washed successively with saturated sodium bicarbonate and brine. The EtOAc layer was obtained, dried with sodium sulfate, filtered, and concentrated in vacuo. The residue was purified on a silica gel columns using hexanes and ethyl acetate with 0.1% TEA (5:1, 3:1, 1:1 gradient). A mixture of anomers was obtained for each analog. Analogs were purified further by trituration in pure hexanes at 35° C. for 45 minutes, decanting, filtering out the solid, and washing thoroughly with hexanes. Analogs were characterized by $^1$H NMR and $^{13}$C NMR.

Synthesis of 4a: 3a (200 mg) was mixed with activated and crushed molecular sieves 4 Å (1 g) in methanol (50 ml) and stirred at 22° C. The reaction mixture was monitored by TLC (hexanes:EtOAc) to maximize conversion to the 3,4,6-substituted analog while minimizing de-acylation at positions other than C1. After ~36 h, the reaction mixture was filtered through celite, washed twice with methanol (10 ml), and the combined filtrate was concentrated. Column chromatography of the residue (hexanes:ethyl acetate (AcOEt)) was done to separate unreacted starting material, respectively from the hemiacetals to give 4a. The analog was purified further by trituration in pure hexanes at 35° C. for 45 minutes, decanting, filtering out the solid, and washing thoroughly with hexanes.

NMR Data

2a. $^1$H NMR (500 MHz, DEUTERIUM OXIDE) δ 7.70-7.83 (m, 3H), 7.55-7.65 (m, 2H), 7.42-7.55 (m, 4H), 5.31 (d, J=3.46 Hz, 1H), 4.85 (d, J=8.49 Hz, 1H), 4.10 (dd, J=3.54, 10.77 Hz, 1H), 3.86-3.95 (m, 4H), 3.63-3.86 (m, 3H), 3.44-3.60 (m, 2H)

3a. Starting amount 1: 30.0 g. End yield: 10.8 g, 17%. $^1$H NMR (500 MHz, CHLOROFORM-d) δ 7.61-7.76 (m, 3H), 7.37-7.56 (m, 4H), 6.41 (d, J=9.43 Hz, 1H), 6.23-6.37 (m, 2H), 5.81 (d, J=8.80 Hz, 1H), 5.35-5.44 (m, 1H), 5.18-5.35 (m, 2H), 4.65 (ddd, J=3.69, 8.61, 10.96 Hz, 1H), 4.58 (d, J=10.22 Hz, 1H), 4.23-4.37 (m, 1H), 3.98-4.22 (m, 2H), 3.48 (d, J=5.34 Hz, 1H), 2.17 (s, 3H), 2.01-2.14 (m, 13H), 1.99 (s, 1H); $^{13}$C NMR (126 MHz, CHLOROFORM-d) δ 171.9, 171.1, 170.4, 170.4, 169.3, 168.9, 168.8, 168.3, 167.0, 166.8, 133.3, 133.0, 131.8, 131.7, 128.5, 128.5, 126.7, 126.6, 92.6, 90.3, 76.7, 76.5, 72.8, 72.4, 70.5, 69.5, 67.4, 67.1, 61.4, 61.3, 53.1, 51.6, 20.6, 20.6, 20.5, 20.5, 20.4, 20.3

3b. Starting amount 1: 500 mg. End yield: 315 mg, 30.4%. $^1$H NMR (500 MHz, CHLOROFORM-d) δ 7.62-7.74 (m, 2H), 7.47-7.58 (m, 1H), 7.37-7.47 (m, 3H), 6.36 (d, J=3.62 Hz, 1H), 6.21 (d, J=8.80 Hz, 1H), 5.84 (d, J=8.80 Hz, 1H), 5.49 (dd, J=1.26, 3.14 Hz, 1H), 5.32-5.44 (m, 1H), 5.18-5.28 (m, 1H), 4.86-4.97 (m, 1H), 4.24-4.35 (m, 1H), 4.00-4.23 (m, 4H), 2.23 (d, J=2.04 Hz, 1H), 1.99-2.22 (m, 17H), 1.94-1.97 (m, 1H); $^{13}$C NMR (126 MHz, CHLOROFORM-d) δ 171.6, 170.4, 170.2, 168.7, 167.3, 149.5, 136.2, 133.4, 132.0, 128.8, 126.9, 126.9, 93.2, 91.3, 77.3, 76.7, 70.4, 68.6, 67.9, 66.8, 66.4, 61.3, 50.2, 47.8, 20.9, 20.8, 20.8, 20.7, 20.6

3c. Starting amount 1: 500 mg. End yield: 380 mg, 36.7%. $^1$H NMR (500 MHz, CHLOROFORM-d) δ 7.71-7.84 (m, 2H), 7.51-7.63 (m, 1H), 7.39-7.51 (m, 3H), 6.35 (d, J=9.27 Hz, 1H), 6.17 (d, J=1.89 Hz, 1H), 5.43 (dd, J=4.40, 10.22 Hz, 1H), 5.29 (t, J=10.14 Hz, 1H), 4.87 (ddd, J=1.89, 4.36, 9.16 Hz, 1H), 4.28 (dd, J=4.56, 12.42 Hz, 1H), 3.98-4.19 (m, 3H), 2.21 (s, 3H), 2.17 (s, 1H), 1.91-2.14 (m, 14H); $^{13}$C NMR (126 MHz, CHLOROFORM-d) δ 170.4, 170.1, 169.6, 168.1, 167.5, 133.7, 132.1, 128.8, 128.7, 127.0, 127.0, 91.6, 77.3, 76.7, 70.1, 69.0, 65.4, 62.0, 60.4, 49.6, 21.0, 20.9, 20.7, 20.7, 20.6, 14.2

3d. Starting amount 1: 750 mg. End yield: 636 mg, 46.3%. $^1$H NMR (500 MHz, CHLOROFORM-d) δ 6.02 (d, J=1.73 Hz, 1H), 5.81-5.92 (m, 1H), 5.33 (dd, J=4.56, 10.22 Hz, 1H), 5.02-5.21 (m, 1H), 4.77 (ddd, J=1.73, 3.93, 9.12 Hz, 1H), 4.64 (ddd, J=1.81, 4.52, 9.24 Hz, 1H), 4.21-4.33 (m, 1H), 3.98-4.16 (m, 3H), 3.76-3.84 (m, 1H), 2.17 (s, 3H), 1.94-2.14 (m, 13H); $^{13}$C NMR (126 MHz, CHLOROFORM-d) δ 171.2, 170.6, 170.2, 170.1, 170.0, 169.7, 168.2, 91.8, 90.7, 77.3, 77.1, 76.8, 73.5, 71.4, 70.1, 68.8, 65.6, 65.3, 62.1, 62.0, 60.4, 49.5, 49.3, 21.1, 20.9, 20.8, 20.7, 20.7, 20.7, 14.2

4a. Starting amount 3a: 200 mg. End yield: 117.3 mg, 63.6%. $^1$H NMR (500 MHz, CHLOROFORM-d) δ 7.68-7.78 (m, 3H), 7.37-7.58 (m, 5H), 6.53 (d, J=9.12 Hz, 1H), 5.38-5.50 (m, 2H), 5.11-5.28 (m, 1H), 4.50 (ddd, J=3.46, 9.12, 10.85 Hz, 1H), 4.09-4.32 (m, 4H), 1.96-2.20 (m, 13H); $^{13}$C NMR (126 MHz, CHLOROFORM-d) δ 171.5, 170.6, 169.1, 167.1, 133.3, 131.7, 128.6, 128.5, 126.9, 126.7, 91.4, 76.7, 76.5, 76.2, 70.6, 67.8, 67.6, 61.8, 52.7, 20.5, 20.5, 20.4

2) Synthesis of Analogs Via Amide Couplings

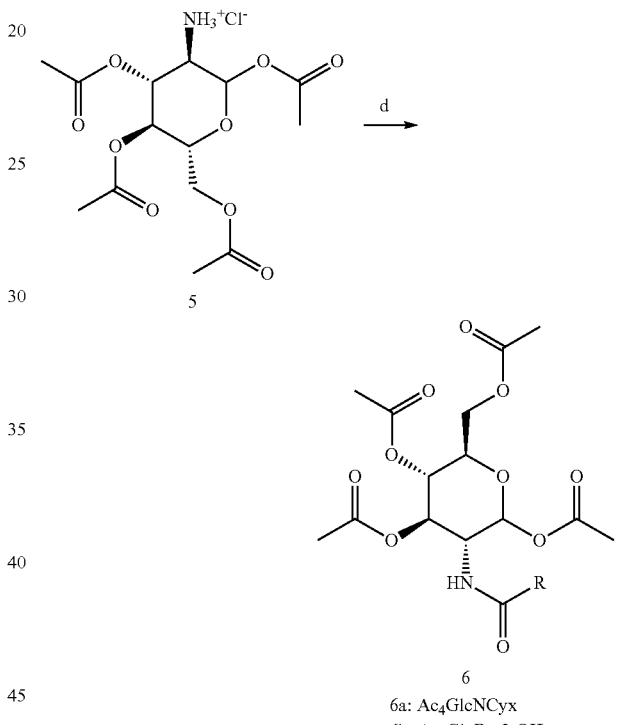

6a: Ac$_4$GlcNCyx
6b: Ac$_4$GlcBz-2-OH

General Scheme for Synthesis of Analogs Via Amide Couplings (6a-b):

1,3,4,6-Tetra-O-acetyl-α-D-glucosamine HCl was stirred in anhydrous THF (10 mL). TBTU was added (2 eq.) followed by DIEA (3 eq.). The reaction was stirred under an inert atmosphere of nitrogen for 10 minutes. The appropriate carboxylic acid (cyclohexane carboxylic acid for 6a, salicylic acid 6b) was dissolved in THF (1.1 eq. carboxylic acid, ~2-3 mL THF) and was added to the reaction mixture. The reaction was stirred overnight at room temperature. The reaction was concentrated in vacuo and was then dissolved in ethyl acetate. The organic solution was then washed with a saturated solution of sodium hydrogen carbonate followed by brine. The organics were dried over sodium sulfate, filtered, and concentrated. The crude residue was then purified on a silica gel column using 0.1% TEA, and hexanes: ethyl acetate.

6a. Starting amount 5: 63.3 mg. End yield: 30.3 mg, 40.4%. $^1$H NMR (500 MHz, CHLOROFORM-d) δ 5.63 (d, J=8.80 Hz, 1H), 5.38 (d, J=9.59 Hz, 1H), 4.99-5.12 (m, 2H), 4.15-4.32 (m, 2H), 4.06 (dd, J=2.20, 12.58 Hz, 1H), 3.72 (ddd, J=2.28, 4.64, 9.43 Hz, 1H), 1.86-2.07 (m, 13H), 1.55-1.76 (m, 5H), 1.53 (br. s., 1H), 1.23-1.32 (m, 2H), 1.09-1.22 (m, 3H); $^{13}$C NMR (126 MHz, CHLOROFORM-d) δ 175.0, 170.2, 169.7, 168.5, 168.2, 91.7, 76.3, 76.0, 75.8, 72.0, 71.5, 66.8, 60.8, 51.5, 44.6, 28.4, 28.4, 24.6, 19.8, 19.7, 19.6, 19.6

6b. Starting amount 5: 200 mg. End yield: 86.7 mg, 35.8%. $^{1}$H NMR (500 MHz, CHLOROFORM-d) δ 11.88 (s, 1H), 7.41 (ddd, J=1.57, 7.11, 8.45 Hz, 1H), 6.99 (dd, J=1.02, 8.41 Hz, 1H), 6.75-6.89 (m, 1H), 6.60 (d, J=9.27 Hz, 1H), 5.81 (d, J=8.65 Hz, 1H), 5.17-5.39 (m, 2H), 4.55 (td, J=8.98, 10.65 Hz, 1H), 4.31 (dd, J=4.72, 12.42 Hz, 1H), 4.18 (dd, J=2.20, 12.42 Hz, 1H), 3.80-3.95 (m, 1H), 1.92-2.16 (m, 13H); $^{13}$C NMR (126 MHz, CHLOROFORM-d) δ 171.5, 170.4, 169.9, 169.3, 169.0, 161.3, 134.6, 125.2, 118.8, 118.4, 113.3, 92.4, 76.7, 76.5, 72.9, 72.2, 67.3, 61.4, 52.7, 20.6, 20.5, 20.4, 20.3

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

A number of embodiments of the invention have been described. Nevertheless, it will be understood that various modifications may be made without departing from the spirit and scope of the invention. Accordingly, other embodiments are within the scope of the following claims.

What is claimed:

1. A method of treating a disease comprising administering to a subject an effective amount of a compound or pharmaceutically acceptable salt, solvate, anomers or hydrate thereof:

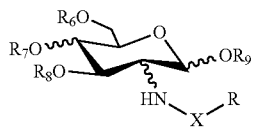

wherein X is CO, SO$_2$ or CH$_2$;
$R_6$, $R_7$, $R_8$, $R_9$, are each independently H or CO(CH$_2$)$_n$CH$_3$;
n is 0-16;
R is

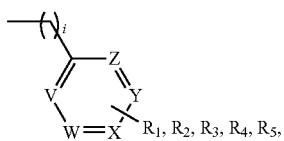

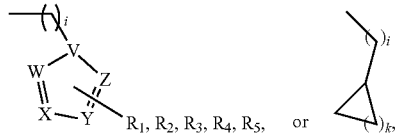

wherein V, W, X, Y, Z are, each independently C or N, $R_1$, $R_2$, $R_3$, $R_4$, $R_5$ are, each independently, absent, —H, —(CH$_2$)$_m$CH$_3$ where m=0-6, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, i is 0, and k is 1 to 10,
wherein the disease is selected from cancer, diabetes, neurodegenerative disease, metabolic disorder, cardiovascular disease, ageing, autoimmunity, metabolic syndrome, eye disease and kidney disease.

2. The method of claim 1, wherein the compound is a UAP inhibitor.

3. The method of claim 1, the subject is an animal or human.

4. The method of claim 1, wherein the subject is identified as suffering from cancer, diabetes, neurodegenerative disease, metabolic disorder, cardiovascular disease, ageing, autoimmunity, metabolic syndrome, eye disease and kidney disease.

5. The method of claim 4, wherein subject is suffering from cancer and the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas.

6. The method of claim 5, wherein the subject is suffering from pancreatic cancer or liver cancer.

7. The method of claim 4, wherein the subject is suffering from a metabolic disorder.

8. The method of claim 7, wherein the subject is suffering from diabetes or obesity.

9. The method of claim 4, wherein the subject is suffering from—a neurological disorder.

10. The method of claim 9, wherein the subject is suffering from Alzheimer's disease.

11. The method of claim 1, wherein the compound is administered to the subject orally, topically, parentally, intravenously or intramuscularly.

12. A method of controlling a glycan production in a cell related to a disease, comprising using a compound or pharmaceutically acceptable salt, solvate, anomers or hydrate thereof:

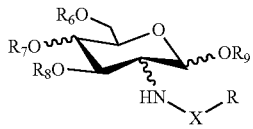

wherein X is CO, SO$_2$ or CH$_2$;

$R_6$, $R_7$, $R_8$, $R_9$, are each independently H or CO(CH$_2$)$_n$CH$_3$;

n is 0-16;

R is

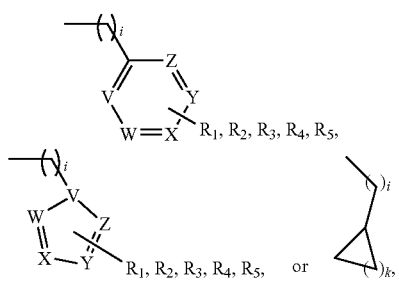

wherein V, W, X, Y, Z are, each independently C or N, $R_1$, $R_2$, $R_3$, $R_4$, $R_5$ are, each independently, absent, —H, —(CH$_2$)$_m$CH$_3$ where m=0-6, —Br, —Cl, —F, —I, —NH$_2$, —SH, —NO$_2$, —NHSO$_2$R$^a$ where IV is alkyl or branched alkyl, —SO$_2$NHR$^b$ where R$^b$ is alkyl or branched alkyl, —OH, —OR$_c$ where R$_c$ is alkyl or branched alkyl or alkyl ester, —NHR$^d$ where R$^d$ is alkyl or branched alkyl or amide, —OCF$_3$, —COOH, or —COOR$^e$ where R$^e$ is alkyl or branched alkyl, i is 0, and k is 1 to 10.

13. The method of claim 12, wherein the compound inhibits UAP activity in hexosamine biosynthesis pathway in the cell.

14. The method of claim 13, wherein the glycan is a disease-promoting glycan.

15. The method of claim 12, wherein the disease is selected from cancer, diabetes, neurodegenerative disease, metabolic disorder, cardiovascular disease, ageing, autoimmunity, metabolic syndrome, eye disease and kidney disease.

16. The method of claim 15, wherein the cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas.

17. The method of claim 16, wherein the disease is pancreatic cancer or liver cancer.

18. A method of treating a brain tumor in a subject comprising administering to the subject an effective amount of a compound or pharmaceutically acceptable salt, solvate, anomers or hydrate thereof:

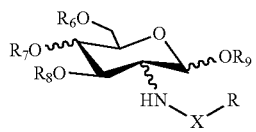

wherein X is CO, SO$_2$ or CH$_2$;

$R_6$, $R_7$, $R_8$, $R_9$, are each independently H or CO(CH$_2$)$_n$CH$_3$;

n is 0-16;

R is

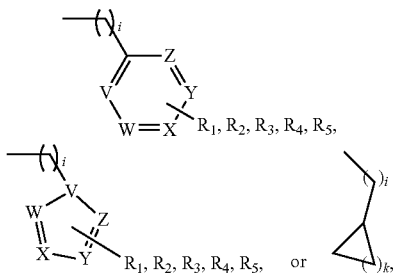

wherein V, W, X, Y, Z are, each independently C or N, $R_1$, $R_2$, $R_3$, $R_4$, $R_5$ are, each independently, absent, —H, —(CH$_2$)$_m$CH$_3$ where m=0-6, —Br, —Cl, —F, —I, —NH$_2$, —SH, —NO$_2$, —NHSO$_2$R$^a$ where R$^a$ is alkyl or branched alkyl, —SO$_2$NHR$^b$ where R$^b$ is alkyl or branched alkyl, —OH, —OR$^c$ where R$^c$ is alkyl or branched alkyl or alkyl ester, —NHR$^d$ where R$^d$ is alkyl or branched alkyl or amide, —OCF$_3$, —COOH, or —COOR$^e$ where R$_e$ is alkyl or branched alkyl, i is 0, and k is 1 to 10.

19. The method of claim 18, wherein the brain tumor is selected from the group consisting of a glioma, a glioblastoma, a meningioma, a chordoma, other tumor of the central nervous system, and a metastatic tumor to the brain.

20. The method of claim 18, the subject is an animal or human.

* * * * *